(12) United States Patent
Pujol Onofre

(10) Patent No.: US 8,865,747 B2
(45) Date of Patent: Oct. 21, 2014

(54) PIOGLITAZONE FOR USE IN THE TREATMENT OF ADRENOLEUKODYSTROPHY

(71) Applicants: Fundació Institut D'Investigació Biomèdica de Bellvitge (IDIBELL), Barcelona (ES); Fundació Institució Catalana de Recerca I Estudis Avançats (ICREA), Barcelona (ES); Fondation ELA, Laxou Cedex (FR)

(72) Inventor: Aurora Pujol Onofre, Barcelona (ES)

(73) Assignees: Fundació Institute D'Investigació Biomèdica de Bellvitge (IDIBELL), Barcelona (ES); Fundació Institució Catalana de Recerca I Estudis Avançats (ICREA), L'Hospitalet de Llobregat, Barcelona (ES); Fondation ELA, Laxou Cedex (ES)

( * ) Notice: Subject to any disclaimer, the term of this patent is extended or adjusted under 35 U.S.C. 154(b) by 0 days.

(21) Appl. No.: 13/799,636

(22) Filed: Mar. 13, 2013

(65) Prior Publication Data

US 2013/0274295 A1  Oct. 17, 2013

Related U.S. Application Data

(60) Provisional application No. 61/646,558, filed on May 14, 2012.

(30) Foreign Application Priority Data

Mar. 23, 2012  (EP) .................................. 12382108

(51) Int. Cl.
*A61K 31/4439* (2006.01)
*A61K 45/06* (2006.01)

(52) U.S. Cl.
CPC ............. *A61K 31/4439* (2013.01); *A61K 45/06* (2013.01)
USPC ........................................................ 514/342

(58) Field of Classification Search
CPC ........................... A61K 31/4439; A61K 45/06
See application file for complete search history.

(56) References Cited

U.S. PATENT DOCUMENTS 6,191,154 B1  2/2001  Landreth et al.

FOREIGN PATENT DOCUMENTS

EP   1133294 B1   8/2010
WO   0032190 A1   6/2000

OTHER PUBLICATIONS

Schätz et al. In Journal of Neuroscience 25(34):7805-7812 (2005).*
Geldmacher et al. In Archives of Neurology 68(1) 45-50 (2011).*
Fourcade et al. In Human Molecular Genetics 19(10):2005-2014 (2010).*
Berger et al. In Brain Pathology 20(4):845-856 (2010).*
Mehera et al. In Abstracts of Papers 232nd ACS National Meeting, San Francisco, 2006.*
Berger, Joel, et al.; "The Mechanisms of Action of PPARs," Annu. Rev. Med., 2002, pp. 409-435, vol. 53.
Bogacka, Iwona, et al.; "Pioglitazone Induces Mitochondrial Biogenesis in Human Subcutaneous Adipose Tissue In Vivo," Diabetes, 2005, pp. 1392-1399, vol. 54.
Collino, Massimo, et al.; "Modulation of the oxidative stress and inflammatory response by PPAR-gamma agonists in the hippocampus of rats exposed to cerebral ischemia/reperfusion," European Journal of Pharmacology, 2006, pp. 70-80, vol. 530.
Feinstein, Douglas L., et al.; "Peroxisome Proliferator-Activated Receptor-gamma Agonists Prevent Experimental Autoimmune Encpehalomyelitis," Ann. Neurol, 2002, pp. 694-702, vol. 51.
Ghosh, Sangeeta, et al.; "The Thiazolidinedione Pioglitazone Alters Mitochondrial Function in Human Neruon-Like Cells," Molecular Pharmacology, 2007, pp. 1695-1702, vol. 71.
Gray, Elizabeth, et al.; "The PPAR-gamma agonist pioglitazone protects cortical neurons from inflammatory mediators via improvement in peroxisomal function," Journal of Neuroninflammation, 2012, pp. 1-12, vol. 9.
Heneka, Michael T., et al.; "Acute treatment with the PPARgamma agonist pioglitazone and ibuprofen reduces glial inflammation and ABeta1-42 levels in APPV717I Transgenic mice," Brain, 2005, pp. 1442-1453, vol. 128.
Heneka, Michael T., et al.; "PPARs in the brain," Biochimica et Biophysica Acta, 2007, pp. 1031-1045, vol. 1771.
Kassmann, Celia M., et al.; "A role for myelin-associated peroxisomes in maintaining paranodal loops and axonal integrity," FEBS Letters, 2011, pp. 2205-2211, vol. 585.
Miglio, Gianluca, et al.; "PPARgamma stimulation promotes mitochondrial biogenesis and prevents glucose deprivation-induced neuronal cell loss," Neurochemistry International, 2009, pp. 496-504, vol. 55.
The Myelin Project, Newsletter, The Year in Review, 2010.
The Myelin Project, Newsletter, The Year in Review, 2011.
Rahimian, Reza, et al.; "Effect of Pioglitazone on Sciatic Nerve Ischemia/Reperfusion Injury in Rats," Pediatric Neurosurgery, 2009, pp. 126-131, vol. 45.
Schutz, Burkhard, et al.; "The Oral Antidiabetic Pioglitazone Protects from Neurodegeneration and Amyotrophic Lateral Sclerosis-Like Symptoms in Superoxide Dismutasse-G93A Transgenic Mice," Journal of Neuroscience, 2005, pp. 7805-7812, vol. 25.
Tontonoz, Peter, et al.; "Fat and Beyond: The Diverse Biology of PPARgamma," Annu. Rev. Biochem., 2008, pp. 289-312, vol. 77.
http://www.myelin.org/2008-news-from-the-laboratory/.

* cited by examiner

*Primary Examiner* — Dennis Heyer
(74) *Attorney, Agent, or Firm* — Tristan A. Fuierer; Moore & Van Allen, PLLC

(57) ABSTRACT

The present invention is directed to pioglitazone, or a pharmaceutically acceptable salt thereof, as well as a pharmaceutical composition comprising pioglitazone, or a pharmaceutically acceptable salt thereof, and a pharmaceutically acceptable excipient, for use in the treatment and/or prevention of an adrenoleukodystrophy.

11 Claims, 14 Drawing Sheets

PIOGLITAZONE FOR USE IN THE TREATMENT OF ADRENOLEUKODYSTROPHY

CROSS-REFERENCE TO RELATED APPLICATIONS

This application claims priority under 35 U.S.C. §119(a) to European Patent Application No. EP12382108.4, filed Mar. 23, 2012 and entitled "Pioglitazone for Use in the Treatment of Adrenoleukodystrophy" in the name of Aurora PUJOL ONOFRE and under 35 U.S.C. §119(e) to U.S. Provisional Patent Application No. 61/646,558, filed May 14, 2012 and entitled "Pioglitazone for Use in the Treatment of Adrenoleukodystrophy" in the name of Aurora PUJOL ONOFRE, both of which are incorporated by reference herein in their entirety.

FIELD OF THE INVENTION

The present invention is directed to pioglitazone or a pharmaceutically acceptable salt thereof for use in the treatment and/or prevention of an adrenoleukodystrophy.

BACKGROUND

Adrenoleukodystrophy (X-linked adenoleukodystrophy or X-ALD) is a rare, inherited disorder that leads to progressive damage to the brain, adrenal gland, peripheral nervous system, and eventually death. ALD belongs to the group of generic disorders called leukodystrophies, whose main feature is damage to myelin.

X-ALD presents three main phenotypes: (i) an adult adrenomyeloneuropathy (AMN) with axonopathy in spinal cords, (ii) cerebral adrenomyeloneuropathy with brain demyelination (cAMN), and (iii) childhood variant (cALD) characterized by severe cerebral demyelination.

X-ALD is the most frequently inherited leukodystrophy, with a minimum incidence of 1 in 17,000 males. The gene mutated in the disease (ABCD1) encodes for the ABCD1 protein, an ATP binding cassette transporter and an integral peroxisomal membrane protein involved in the import of very long-chain fatty acids (VLCFA, C≥22:0) and VLCFA-CoA esters into the peroxisome for degradation [Hetterm E. H. et al., *Embo J.* 1996, 15, 3813-3822; and van Roermund C. W. et al., *Faseb J.* 2008, 22, 4201-4208]. The defective function of the ABCD1 transporter leads to VLCFA accumulation in most organs and plasma.

Approximately 70% of male X-ALD patients develop primary adrenocortical insufficiency. In affected patients, adrenal hormone replacement therapy is mandatory and effective. However, this therapy does not influence the development or progression of neurological symptoms.

Some dietary treatments, for example, Lorenzo's oil (a 4:1 mixture of glyceryl trioleate and glyceryl trierucate) in combination with a diet low in VLCSFA (very long chain saturated fatty acids), have been used with limited success in the treatment of X-ALD.

To date, therapies targeting the immune system (immunosuppressive and/or immunomodulating) have not proven to be successful.

Lovastatin, an anti-cholesterol drug, appears to have some effect in vitro, but not in mice with the animal model of adrenoleukodystrophy [Yamada T. et al., *J. Inherit. Metab. Dis.* 2000, 23, 607-614].

Another therapeutic strategy is based on the use of histone deacetylase (HDAC) inhibitors 4-phenylbutyrate (4-PBA) and valproic acid (VPA). The poor response of 4-PBA was suggested to be caused by its short half-life and its capacity of inducing tachyphylaxis. The use of VPA for the treatment and/or prevention of X-ALD is described in ES 2303441 B1. However, its efficacy in improving the clinical symptoms of human patients has not been tested. Further, in a recent study in X-ALD patients, adverse effects such as trembling have been detected, which worsen the symptoms of the disease.

Currently, c-ALD can be treated by bone marrow transplant (BMT) from an allogeneic donor, or by infusion of genetically modified bone marrow cells that, within the brain, abrogate the aggressive microglia-based inflammatory reaction to the excess of VLCFA [Cartier N. et al., *Science* 2009, 326, 818-823]. However, BMT carries an elevated risk of mortality and morbidity, and the gene therapy approach is still at the early experimental stages. Both treatments can only be applied at the very first signs of disease, which means that most cALD patients do not have a valid therapeutic option.

There is no cure yet for AMN, although a clinical trial is ongoing to test the effect of an antioxidant treatment (NCT01495260). The chosen protocol is based on a wealth of studies in patients as well as in the mouse models of the disease that, taken together, extensively document that a complex interplay of oxidative stress and bioenergetic failure underlies the damaging effects of VLCFA [Lopez-Erauskin J. et al., *Ann. Neurol.* 2011, 70, 84-92; Fourcade S. et al., *Hum. Mol. Genet.* 2008, 17, 1762-1773; and Galino J. et al., *Antioxid. Redox Signal* 2011, 15, 2095-2107]. Recently, the use of a combination of N-acetylctysteine (NAC) and alpha lipoic acid (LA) has been disclosed as antioxidant therapy for the treatment and/or prevention of X-ALD in patent application WO 2011/144777 A1.

In view of the above, there is a need for new therapies for the treatment and/or prevention of X-ALD that overcome the previously mentioned drawbacks of the state of the art.

Pioglitazone is a drug of the class of thiazolidinediones or glitazones that shows hypoglycemic action. This compound is marketed under the tradename Actos® (Takeda Pharmaceuticals) as the monohydrochloride salt of the racemic mixture, for use in the treatment of diabetes mellitus type 2. Pharmacological studies indicate that Actos® improves sensitivity to insulin in muscle and adipose tissue and inhibits hepatic gluconeogenesis, and improves glycemic control while reducing circulating insulin levels. Pioglitazone is a chiral compound whose two enantiomers interconvert in vivo. Further no differences were found in the pharmacologic activity between the two enantiomers. Pioglitazone is a potent agonist for peroxisome proliferator-activated receptor-gamma (PPARγ). PPAR receptors are found in tissues important for insulin action such as adipose tissue, skeletal muscle, and liver. Activation of PPARγ nuclear receptors modulates the transcription of a number of insulin responsive genes involved in the control of glucose and lipid metabolism. Pioglitazone was disclosed for the first time in the patent family corresponding to EP 0 193 256 A1 as a therapeutic agent for diabetes and hyperlipemia.

The inventors have surprisingly found that pioglitazone can be used in the treatment and/or prevention of X-ALD.

SUMMARY OF THE INVENTION

The first aspect of the present invention relates to pioglitazone, or a pharmaceutically acceptable salt thereof, for use in the treatment and/or prevention of adrenoleukodystrophies. The second aspect of the present invention relates to a pharmaceutical composition comprising pioglitazone, or a pharmaceutically acceptable salt thereof, and a pharmaceutically acceptable excipient, for use according to the previous aspect.

DESCRIPTION OF THE FIGURES

FIG. 1 shows the mitochondrial DNA (mtDNA) content in spinal cord of

Abcd1-null mice at 12 months of age expressed as the ratio of mtDNA (cytochrome b (Cyt b)) to nuclear DNA (CCAAT/enhancer-binding protein alpha (Cebpα)). N=10/genotype. Statistical analysis was done by Student's t-test: *P<0.05, P<0.01, *P<0.001.

Figure 2:
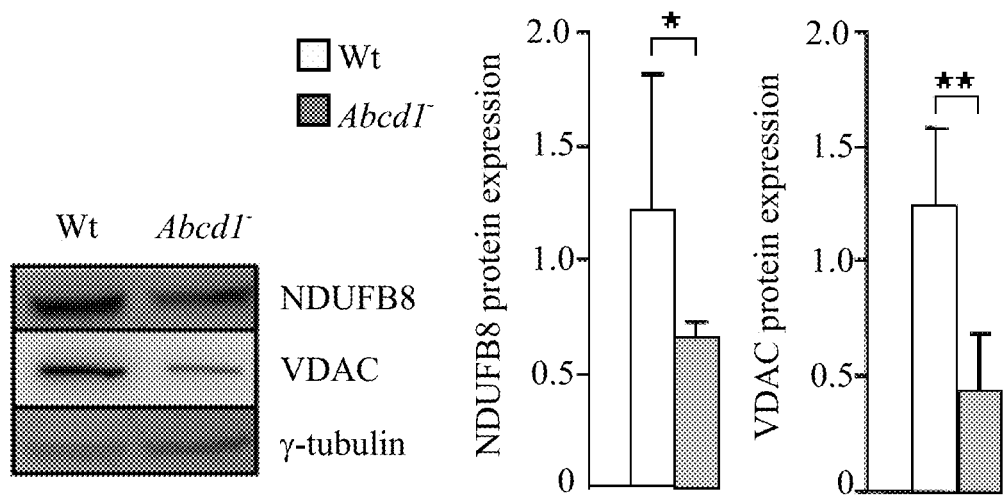

FIG. 2 shows the NADH dehydrogenase ubiquinone 1 beta subcomplex subunit 8 (NDUFB8) and voltage-dependent anion channel (VDAC) expression in spinal cord of Abcd1-null mice at 12 months of age. Representative blots are shown. Protein level is expressed as a percentage of control, and referred to γ-tubulin as loading marker. N=10/genotype. Statistical analysis was done by Student's t-test: *P<0.05, P<0.01, *P<0.001.

Figure 3:
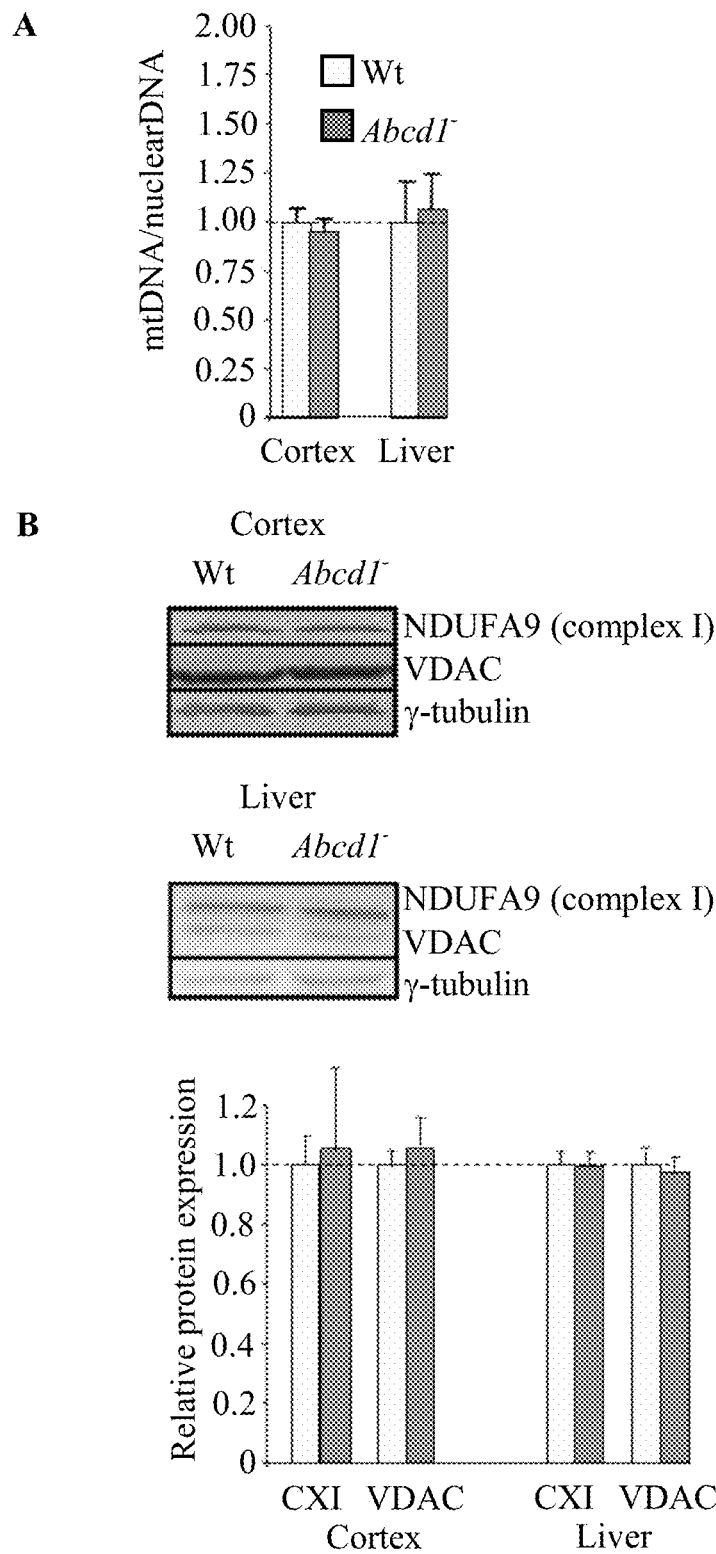

FIG. 3 shows A) mtDNA content expressed as the ratio of mtDNA (Cyt b) to nuclear DNA (Cebpα) (n=8/genotype) in cortex and liver from wild type (WT) and Abcd1-null mice at 12 months of age; B) NDUFA9 (Complex I) and VDAC proteins expression in mouse cortex and liver in cortex and liver from WT and Abcd1-null mice at 12 months of age. Western blots to monitor protein levels have been performed on whole spinal cord lysates in WT and Abcd1$^-$ mice at 12 months of age (n=6/genotype). Representative blots are shown. Protein level is expressed as a percentage of control, and referred to γ-tubulin as loading marker.

Figure 4:
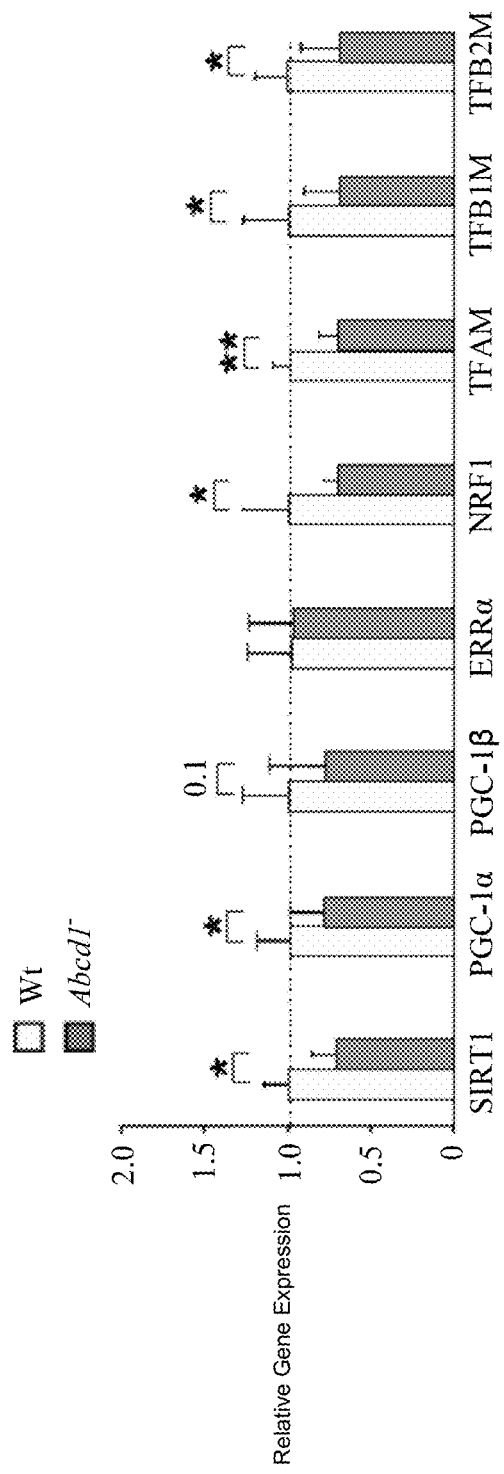

FIG. 4 shows the relative gene expression of SIRT1 (sirtuin 1), PGC-1α (Peroxisome proliferator-activated receptor gamma coactivator 1-alpha), PGC-1β (Peroxisome proliferator-activated receptor gamma coactivator 1-beta), ERRα (estrogen-related receptor alpha), NRF1 (nuclear respiratory factor 1), TFAM (transcrition factor A, mitochondrial), TFB1M (dimethyladenosine transferase 1, mitochondrial), TFB2M (dimethyladenosine transferase 2, mitochondrial) in spinal cord of Abcd1-null mice at 12 months of age. N=10/genotype. Statistical analysis was done by Student's t-test: *P<0.05, P<0.01, *P<0.001.

Figure 5:
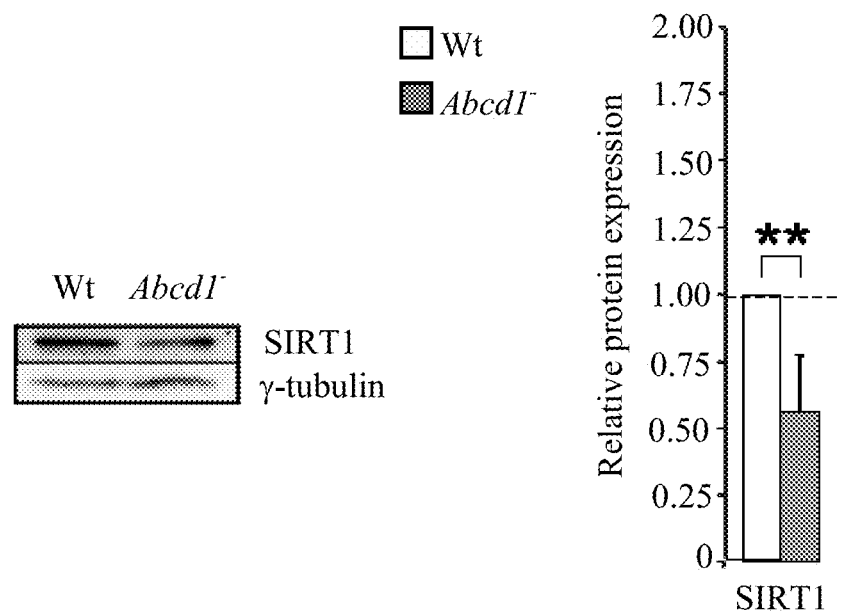

FIG. 5 shows relative SIRT1 protein expression in spinal cord of Abcd1-null mice at 12 months of age. N=10/genotype. Statistical analysis was done by Student's t-test: *P<0.05, P<0.01, *P<0.001.

Figure 6:
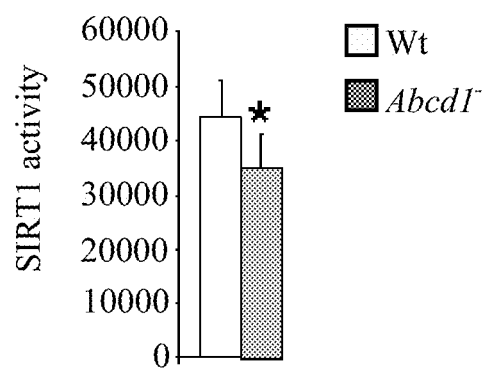

FIG. 6 shows the SIRT1 activity expression in spinal cord of Abcd1-null mice at 12 months of age. N=10/genotype. Statistical analysis was done by Student's t-test: *P<0.05, P<0.01, *P<0.001.

Figure 7:
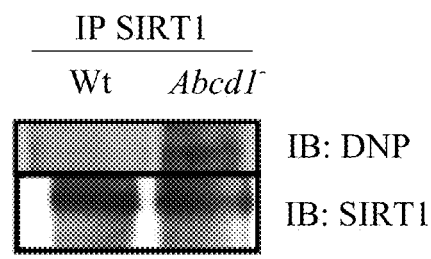

FIG. 7 shows the SIRT1 oxidation levels in spinal cord of Abcd1-null mice at 12 months of age. N=10/genotype. IP is immunoprecipitation and IB is immunoblotting.

Figure 8:
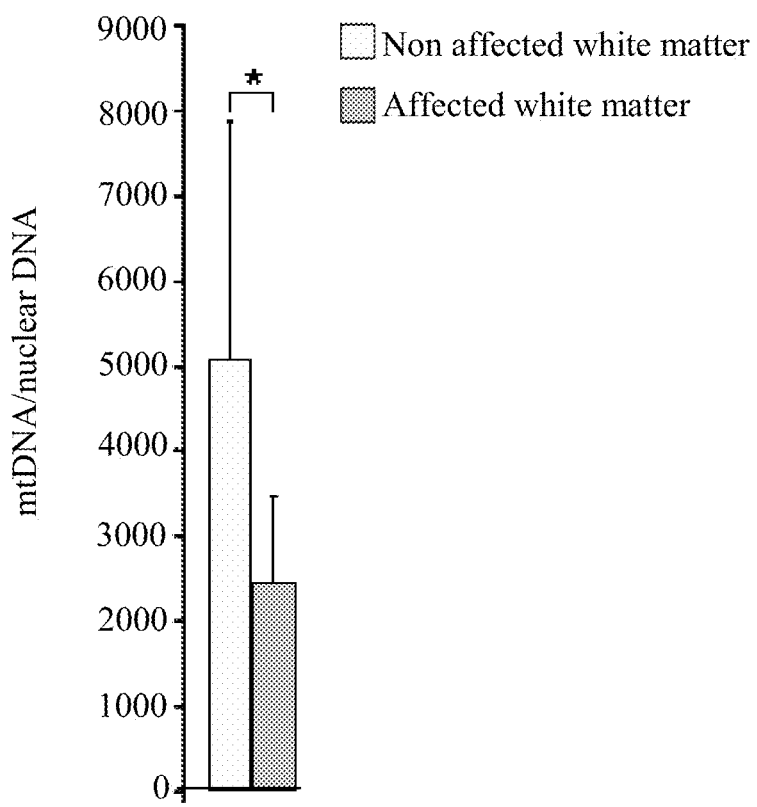

FIG. 8 shows mtDNA content expressed as the ratio of mtDNA (cytochrome c oxidase subunit II, COXII) to nuclear DNA (CEBPα) in affected and normal appearing white matter of X-ALD patients (n=9/condition). Statistical analysis was done by Student's t-test: *P<0.05, P<0.01, *P<0.001.

Figure 9:
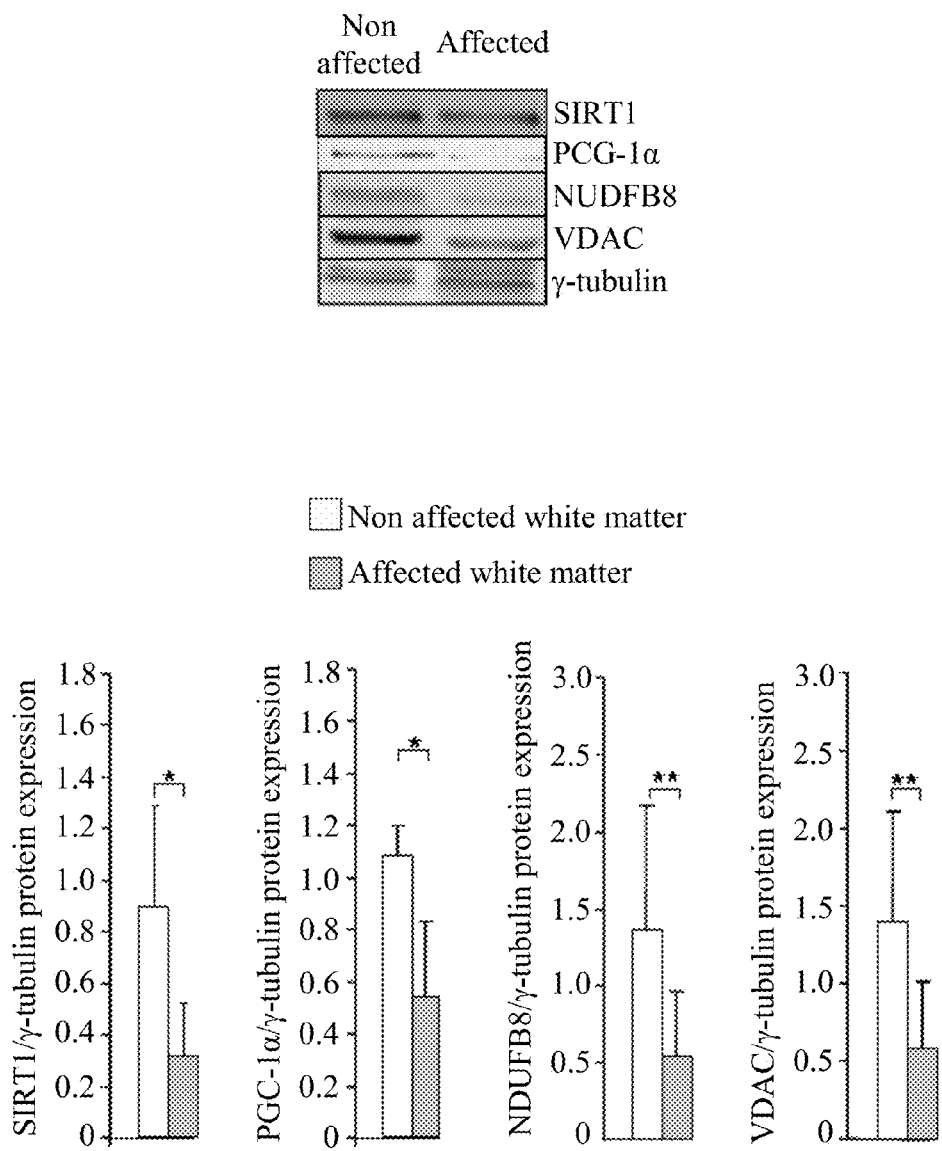

FIG. 9 shows SIRT1, PGC-1α, NDUFB8 and VDAC protein levels in affected and normal appearing white matter of X-ALD patients (n=9/condition). Representative western blots are shown. Protein levels are referred to γ-tubulin as internal loading control. Statistical analysis was done by Student's t-test: *P<0.05, P<0.01, *P<0.001.

Figure 10:
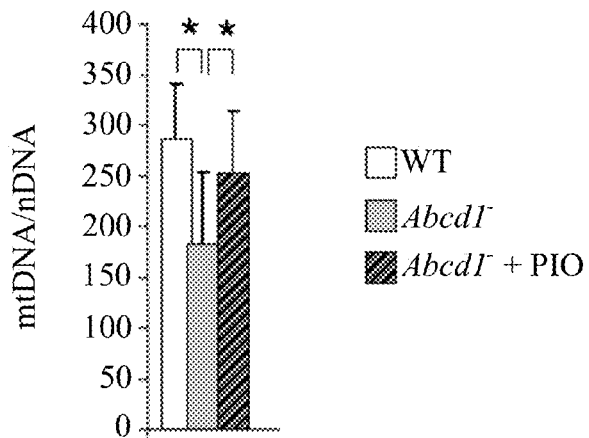

FIG. 10 shows mtDNA content in spinal cord of Abcd1-null mice. Control (n=8), Abcd1$^-$ (n=8) and Abcd1$^-$ mice fed for 2 months with pioglitazone (Abcd1$^-$+PIO) (n=8) at 12 months of age. Data are expressed as mean±SD. Statistical analysis was done by ANOVA followed by Tukey's posthoc test (*p≤0.05, p≤0.01, *p≤0.001).

Figure 11:
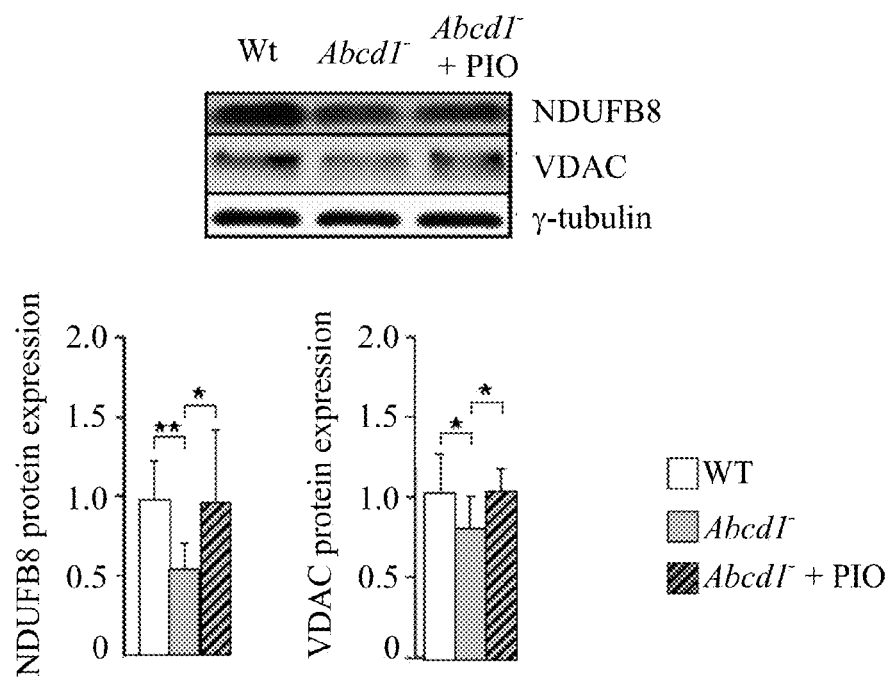

FIG. 11 shows NDUFB8 and VDAC protein levels in spinal cord of Abcd1-null mice. Control (n=8), Abc1$^-$ (n=8) and Abcd1$^{31}$ mice fed for 2 months with pioglitazone (Abcd1$^-$+PIO) (n=8) at 12 months of age. Data are expressed as mean±SD. Statistical analysis was done by ANOVA followed by Tukey's posthoc test (*p≤0.05, p≤0.01, *p0.001).

Figure 12:
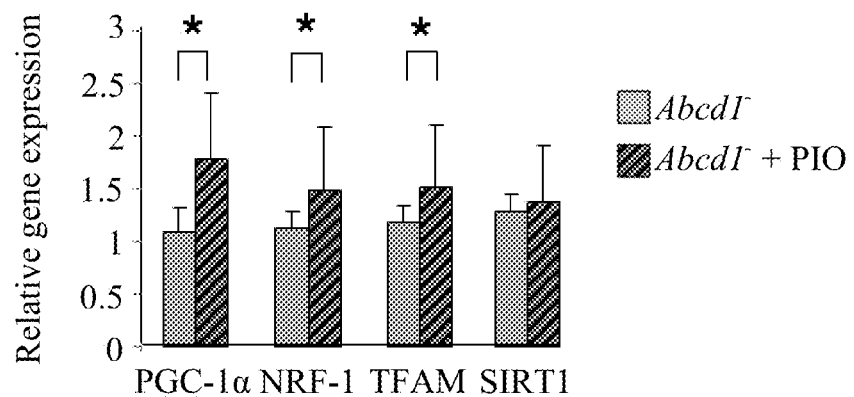

FIG. 12 shows relative gene expression of SIRT1, PGC-1α, TFAM, and NRF1 in spinal cord of Abcd1-null mice. Abcd1$^-$ (n=8) and Abcd1$^-$ mice fed for 2 months with pioglitazone (Abcd1$^-$+PIO) (n=8) at 12 months of age. Data are expressed as mean±SD. Statistical analysis was done by ANOVA followed by Student's t-test (*p≤0.05, p≤0.01, *p≤0.001).

Figure 13:
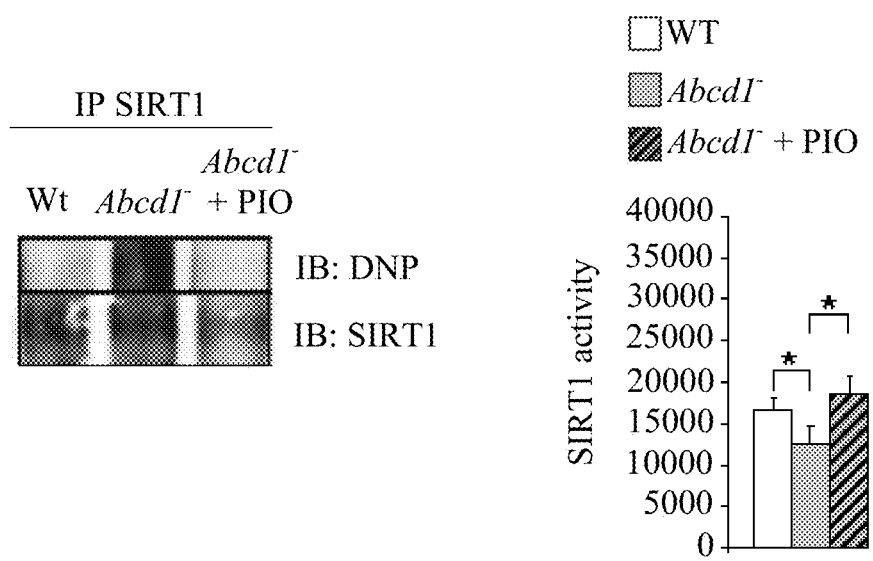

FIG. 13 shows SIRT oxidation levels and SIRT1 activity in spinal cord of Abcd1-null mice. Control (n=8), Abcd1$^{31}$ (n=8) and Abcd1$^-$ mice fed for 2 months with pioglitazone (Abcd1$^{31}$+PIO) (n=8) at 12 months of age. Data are expressed as mean±SD. Statistical analysis was done by ANOVA followed by Tukey's posthoc test (*p≤0.05, p≤0.01, *p≤0.001).

Figure 14:
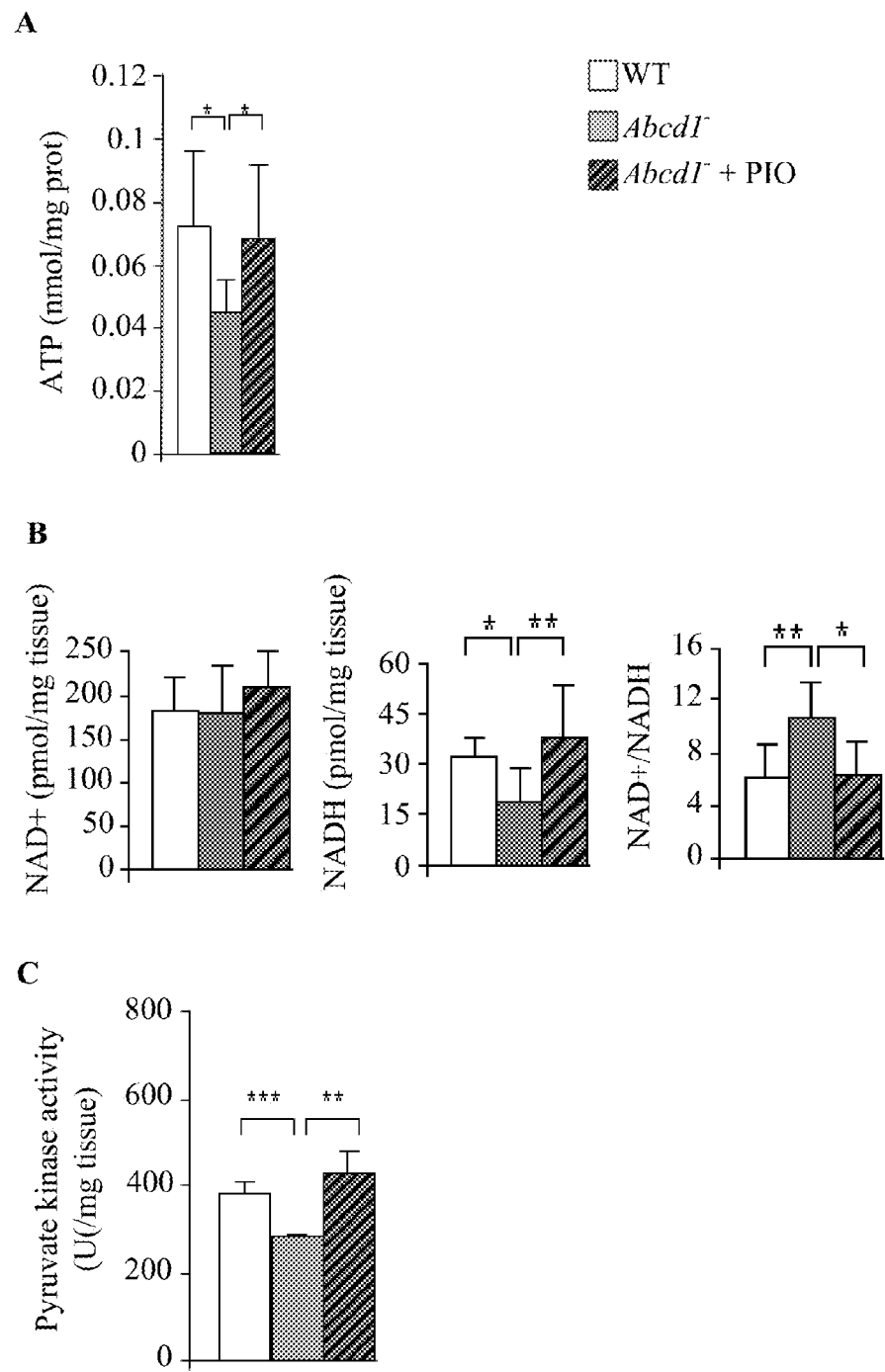

FIG. 14 shows ATP and NADH levels and pyruvate kinase activity in spinal cord of Abcd1-null mice. Control (n=8), Abcd1$^-$ (n=8) and Abcd1$^-$ mice fed for 2 months with pioglitazone (Abcd1$^-$+PIO) (n=8) at 12 months of age. A) ATP; B) NAD+ and NADH levels; and C) pyruvate kinase activity were quantified in spinal cord from WT and Abcd1$^-$ mice (n=6 animals/group). Data represents mean±SD. Statistical analysis was done by ANOVA followed by Tukey's posthoc test (* p<0.05, **p<0.01).

Figure 15:
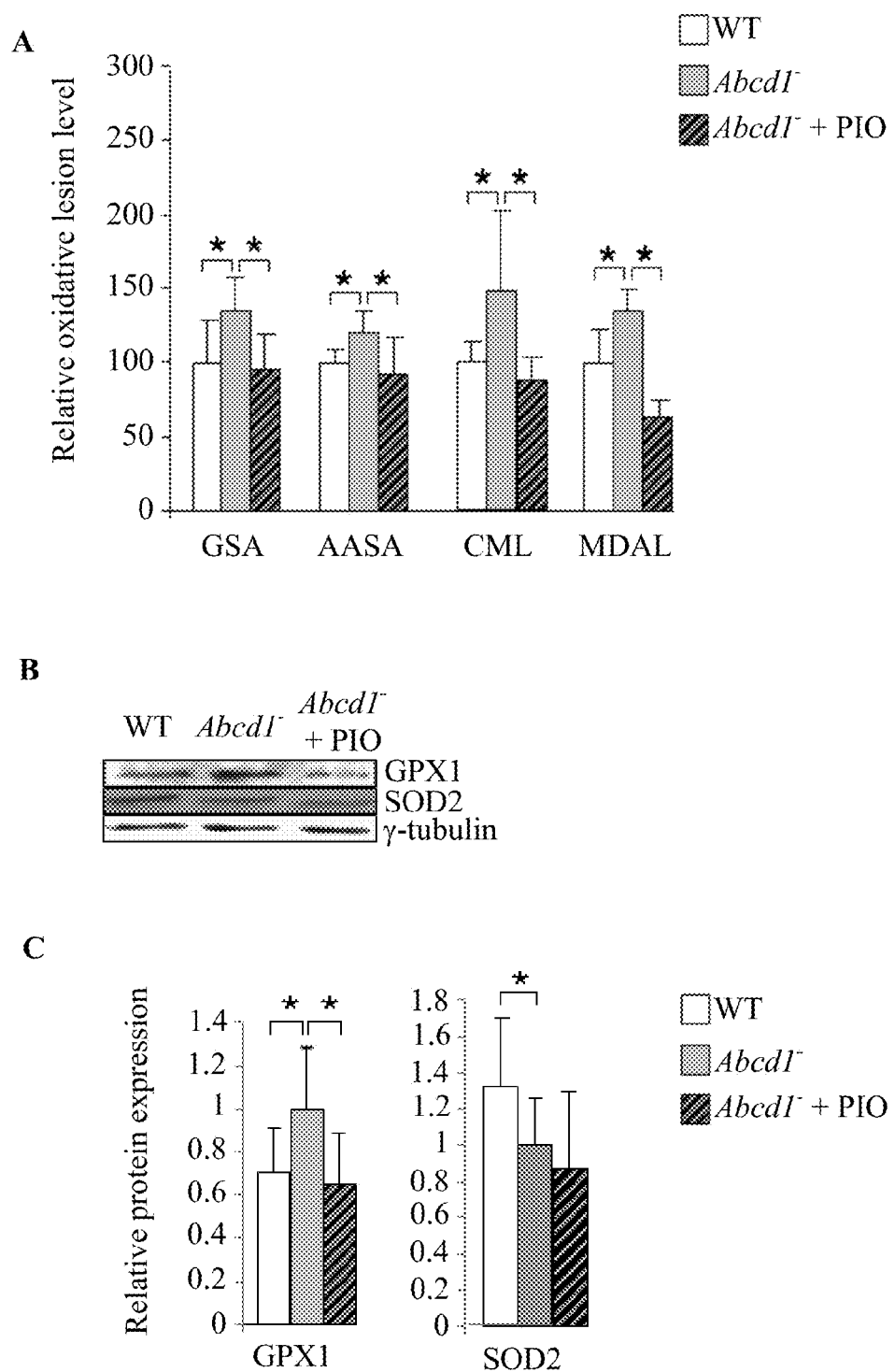

FIG. 15 shows oxidative lesions in Abcd1-null mice. Control (n=8), Abcd1$^-$ (n=8) and Abcd1$^-$ mice fed for 2 months with pioglitazone (Abcd1$^-$+PIO) (n=8) at 12 months of age. A) GSA, AASA, CML and MDAL were quantified by gas chromatography/mass spectrometry (GC/MS); B) GPX1 and SOD2 protein levels. Statistical analysis was done by ANOVA followed by Tukey's posthoc test (*p<0.05).

Figure 16:
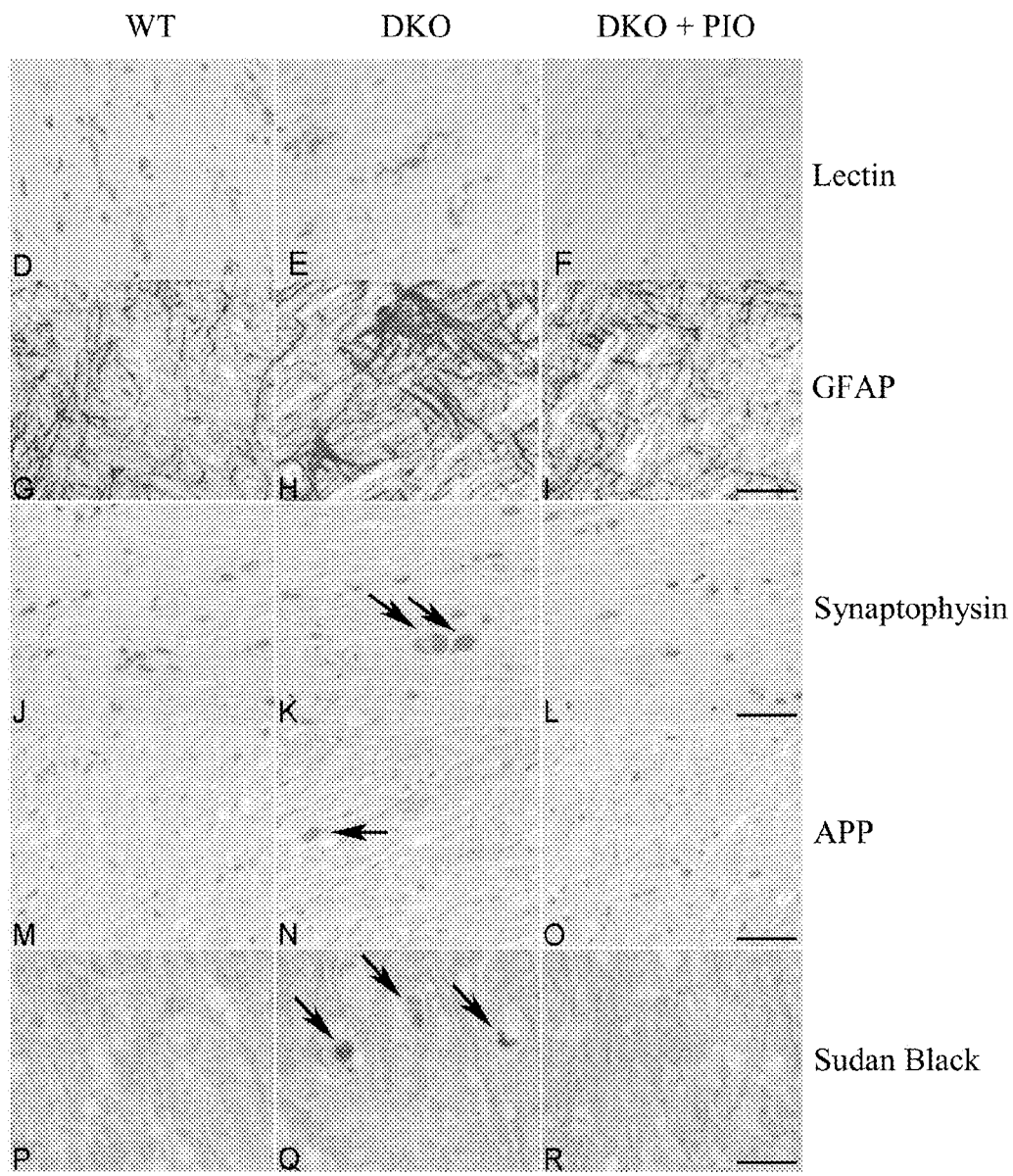

FIG. 16 shows longitudinal sections of the dorsal spinal cord in WT (D, G, J, M, P), Abcd1$^-$/Abcd2$^{-/-}$ (DKO) (E, H, K, N, Q) and Abcd1$^-$/Abcd2$^{-/-}$ treated with pioglitazone (DKO+PIO) (F, I, L, O, R) mice processed for, lectin Lycopericon esculenturn (D-F), GFAP (G-I), synaptophysin (J-L), APP (M-O) and Sudan black (P-R). Bar=25 μm.

Figure 17:
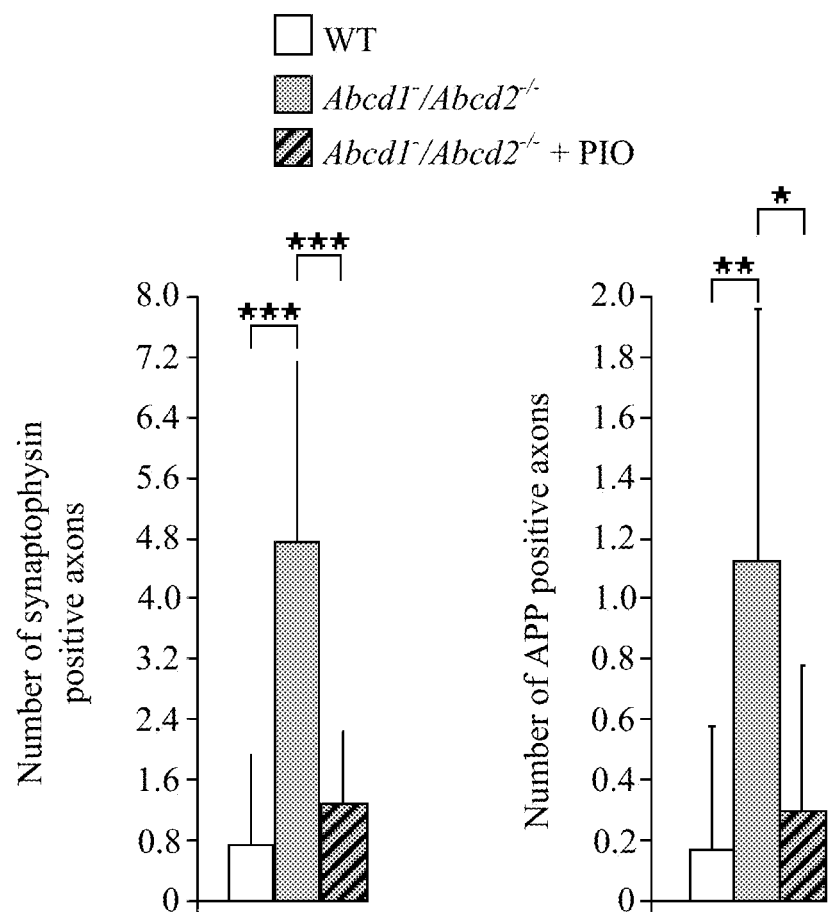

FIG. 17 shows the quantification of APP and synaptophysin accumulation in axonal swellings in WT, DKO and DKO+PIO mice. Significant differences were determined as described in materials and methods (n=5-6 mice per genotype and condition; *P<0.05, P<0.01, *P<0.001).

Figure 18:
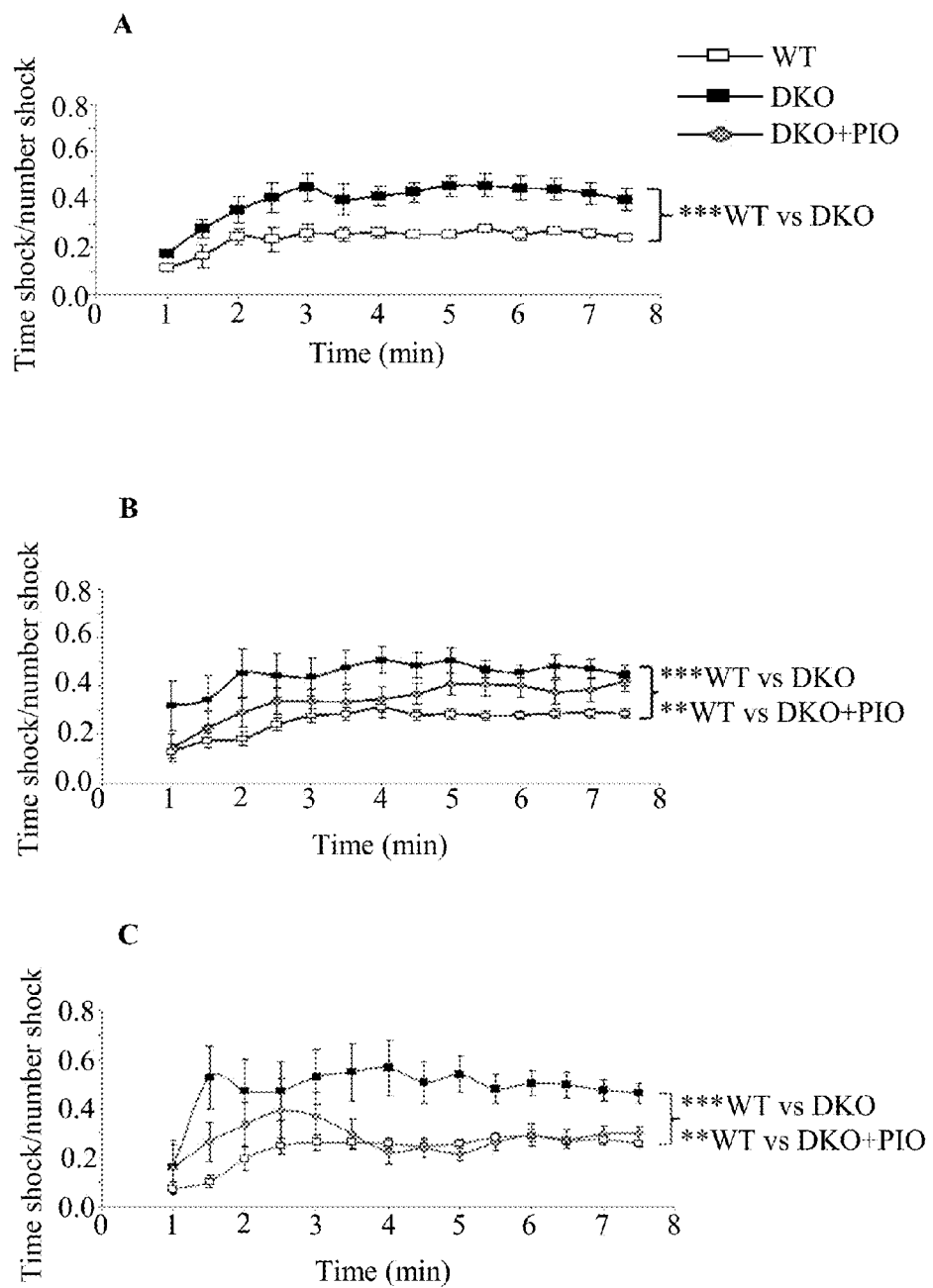

FIG. 18 shows treadmill experiments in WT and Abcd1$^-$/Abcd2$^{-/-}$ mice (DKO) mice at: A) 13 months old mice (before treatment), B) 15 months old mice after 2 months of pioglitazone treatment (DKO+PIO), and C) 17 months old mice after 4 months of pioglitazone treatment (DKO+PIO). Data represents mean±SEM. Statistical analysis was done by ANOVA followed by Tukey's posthoc test (* p≤0.05, p≤0.01*p≤0.001).

Figure 19:
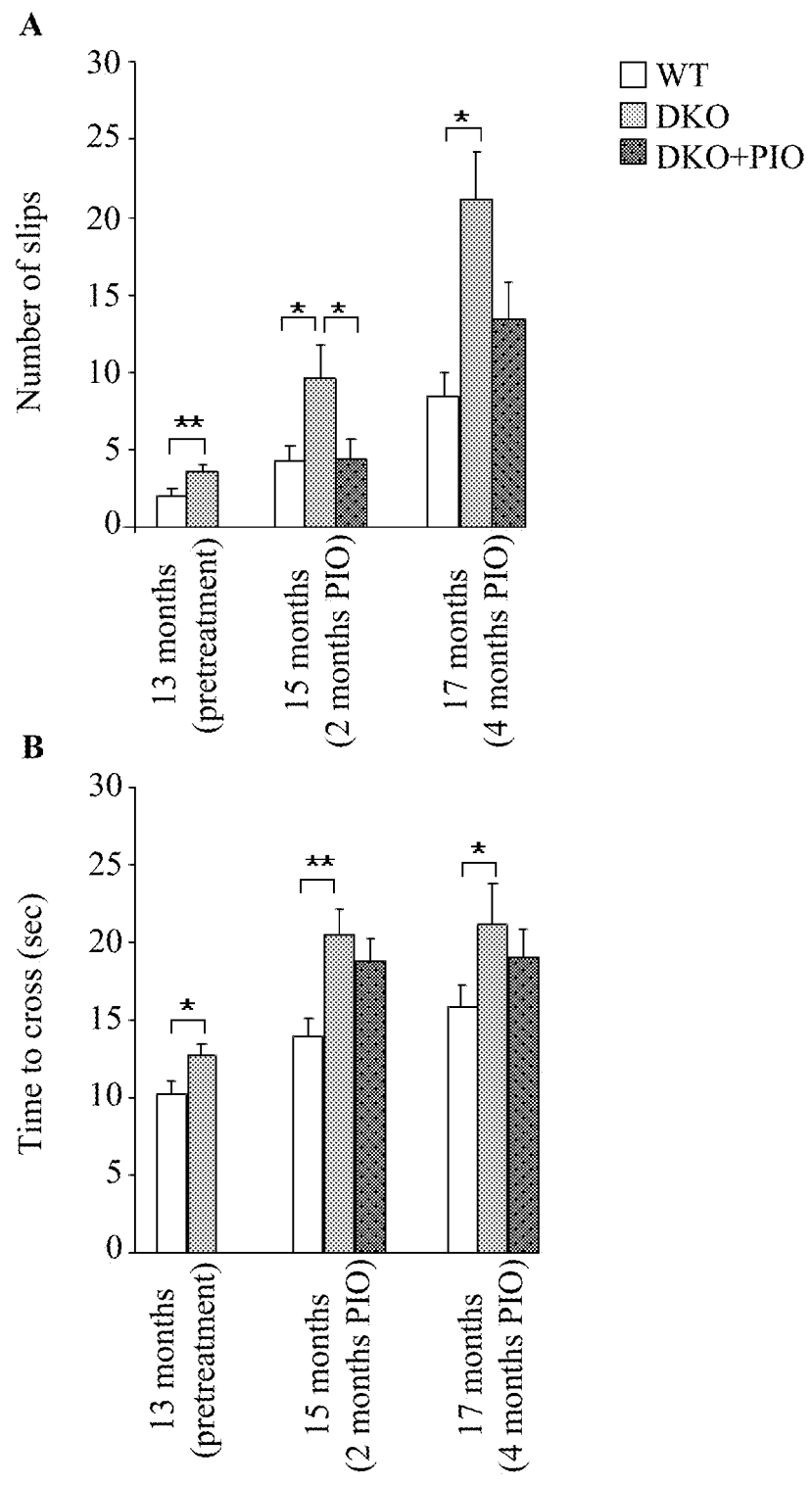

FIG. 19 shows bar-cross experiments in WT and Abcd1$^-$/Abcd2$^{-/-}$ mice (DKO) mice at 13 months old mice (before treatment), 15 months old mice after 2 months of pioglitazone treatment (DKO+PIO), and 17 months old mice after 4 months of pioglitazone treatment (DKO+PIO) represented as: A) number of slips and B) time to cross. Data represents mean±SEM. Statistical analysis was done by ANOVA followed by Tukey's posthoc test (* p≤0.05, p≤0.01*p≤0.001).

DESCRIPTION OF THE INVENTION

Use of Pioglitazone

The first aspect of the present invention relates to pioglitazone, or a pharmaceutically acceptable salt thereof, for use in the treatment and/or prevention of adrenoleukodystrophies.

Pioglitazone is 5-(4-[2-(5-ethylpyridin-2-yl)ethoxy]benzyl)thiazolidine-2,4-dione of formula (I).

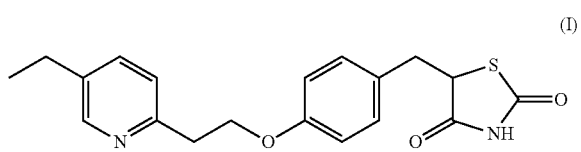 [SMILES: CCc1ccc(CCOc2ccc(CC3SC(=O)NC3=O)cc2)nc1]

In the context of the present invention, pioglitazone refers both to the R enantiomer, and to the S enantiomer, as well as to any mixture thereof such as a racemic mixture of a mixture comprising the two enantiomers at any ratio of the R and S enantiomers of 5-(4-[2-(5-ethylpyridin-2-yl)ethoxy]benzyl)thiazolidine-2,4-dione, such R/S ratio ranging from 1:99 to 99:1, preferably from 20:80 to 80:20, even more preferably form 40:60 to 60:40, even more preferably from 45:55 to 55:45, even more preferably 50:50, as well as to each one of the R or S enantiomer. In a particular embodiment of the invention, pioglitazone refers to the racemic mixture of the R and S enantiomers.

The term "pharmaceutically acceptable salts" refers to any salt, which, upon administration to the recipient is capable of providing (directly or indirectly) a compound as described herein. Preferably, as used herein, the term "pharmaceutically acceptable salt" means approved by a regulatory agency of the Federal or a state government or listed in the U.S. Pharmacopeia or other generally recognized pharmacopeia for use in animals, and more particularly in humans. The preparation of salts can be carried out by methods known in the art.

For instance, pharmaceutically acceptable salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulphonate, p-toluenesulphonate, 2-naphtalenesulphonate, 1,2-ethanedisulphonate. Examples of the alkali addition salts include inorganic salts such as, for example, ammonium, and organic alkali salts such as, for example, ethylenediamine, ethanolamine, N,N-dialkylenethanolamine, triethanolamine, choline, glucamine and basic aminoacids salts. Examples of the metallic salts include, for example, sodium, potassium, calcium, magnesium, aluminium and lithium salts.

Preferably, the pharmaceutically acceptable salt of pioglitazone is selected from the group consisting of hydrochloride, hydrobromide, sulfate, methanesulphonate, p-toluenesulphonate, 2-naphtalenesulphonate, 1,2-ethanedisulphonate, sodium, potassium, calcium, and choline salts. Even more preferably, the pharmaceutically acceptable salt of pioglitazone is the hydrochloride salt.

The term "leukodystrophy" refers to a group of disorders that are characterized by an abnormal formation, turnover, or destruction of myelin. Adrenoleukodystrophy (X-linked adenoleukodystrophy or X-ALD) is a rare, inherited leukodystrophy that leads to progressive damage to the brain, adrenal gland, peripheral nervous system, and eventually death. In a particular embodiment the adrenoleukodystrophy is selected from the group consisting of adult adrenomyeloneuropathy (AMN) with axonopathy in spinal cords, cerebral adrenomyeloneuropathy with brain demyelination (cAMN) and a childhood variant (cALD) characterized by severe cerebral demyelination. In a more preferred embodiment, the adrenoleukodystrophy is adrenomyeloneuropahy (AMN) (i.e. adult adrenomyeloneuropathy with axonopathy in spinal cords).

The term adrenomyeloneuropathy (AMN) as used herein refers to the adult adrenomyeloneuropathy with axonopathy in spinal cords variant of X-ALD.

The terms "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient includes prevention of a particular disorder or adverse physiological event in a susceptible individual as well as treatment of a clinically symptomatic individual.

The terms "prevent" and "prevention" as used herein refer to avoiding the occurrence of a negative event which most likely leads to the worsening of the condition of a patient having a disease, or to the injury or the death of a healthy and/or ill subject.

The term "treatment and/or prevention" in the context of this specification means administration of a pioglitazone, or a pharmaceutically acceptable salt thereof, or pharmaceutical formulation comprising pioglitazone, or a pharmaceutically acceptable salt thereof, to preserve health in a patient suffering or in risk of suffering an adrenoleukodystrophy, preferably adult adrenomyeloneuropathy (AMN), cerebral adrenomyeloneuropathy (cAMN) or the childhood variant of adrenoleukodystrophy (cALD)adrenoleukodystrophy, even more preferably adrenomyeloneuropathy (AMN). Said terms also include administration pioglitazone, or a pharmaceutically acceptable salt thereof, or pharmaceutical formulation comprising pioglitazone, or a pharmaceutically acceptable salt thereof, to prevent, ameliorate or eliminate one or more symptoms associated with an adrenoleukodystrophy, preferably adult adrenomyeloneuropathy (AMN), cerebral adrenomyeloneuropathy (cAMN) or the childhood variant of adrenoleukodystrophy (cALD)adrenoleukodystrophy, even more preferably adrenomyeloneuropathy (AMN).

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

Generally the effective administered amount of pioglitazone, or a pharmaceutically acceptable salt thereof, will depend on the severity of the disorder, or the age, weight or mode of administration. In practice, the physician will determine the actual dosage and administration regimen, which will be the most suitable for the patient suffering or in risk of suffering from an adrenoleukodystrophy, preferably adult adrenomyeloneuropathy (AMN), cerebral adrenomyeloneuropathy (cAMN) or the childhood variant of adrenoleukodystrophy (cALD)adrenoleukodystrophy, even more preferably adrenomyeloneuropathy (AMN). The amount of pioglitazone refers to the amount of free base. Pioglitazone, or a pharmaceutically acceptable salt thereof, will typically be administered once or more times a day, for example 1, 2, 3 or 4 times daily, preferably 3 times daily, with typical total daily doses in the range of from 0.1 to 1.5 mg/kg/day, preferably from 0.5 to 1.0 mg/kg/day, even preferably 0.5 to 0.75 mg/kg/day. The doses are indicated as the daily amount in milligrams of the drug (expressed as mg of pioglitazone free base) administered to the patient by kilogram of weight of such patient.

Another aspect of the present invention relates to a method of treatment or prevention of adrenoleukodystrophies wherein pioglitazone, or a pharmaceutically acceptable salt thereof, is administered to a patient in need thereof.

In one embodiment the method is applied to the treatment or prevention of an adrenoleukodystrophy selected from the group consisting of adult adrenomyeloneuropathy (AMN), cerebral adrenomyeloneuropathy (cAMN) and the childhood variant of adrenoleukodystrophy (cALD), more preferably adult adrenomyeloneuropahy (AMN).

In another embodiment the method of treatment or prevention is characterized by the administration to a patient in need thereof of a dose of pioglitazone, or a pharmaceutically acceptable salt thereof in the range of 0.1 to 1.5 mg/kg/day. In a particular embodiment the method of treatment or prevention is characterized by the administration to a patient in need thereof of a pharmaceutical composition comprising 15 mg, 30 mg or 45 mg of pioglitazone.

Pharmaceutical Compositions

In another preferred embodiment, the invention is directed to pioglitazone, or a pharmaceutically acceptable salt thereof, for use as defined above, in combination with one or more drugs selected from the group consisting of antioxidants, antioxidants targeted to mitochondria, histone deacetylase inhibitors, inhibitors of mitochondria transition pore opening, anti-inflammatory drugs, PPAR agonists, RXR agonists, sirtuin 1 agonists, hypolipidemic agents, and neuroprotector drugs.

"Antioxidants", as used herein, refer to substances that reduce the levels of reactive oxygen species, for instance preventing the formation of such reactive oxygen species or removing them before they produce any damage. Examples of antioxidants are alpha-lipoic acid and N-acetylcisteine.

"Antioxidants targeted to mitochondria", as used herein, refer to those antioxidants that are selectively concentrated within mitochondria in vivo. Examples of antioxidants targeted to mitochondria are mitoquinone (MitroQ) and [2-(3,4-dihydro-6-hydroxy-2,5,7,8-tetramethyl-2H-1-benzopyran-2-yl)ethyl]triphenylphosphonium bromide (MitoVitE).

"Histone deacetylase inhibitors", as used herein, refer to substances that interfere with the function of histone deacetylase. Examples of histone deacetylase inhibitors are vorinostat, romidepsin, panobinostat, valproic acid, belinostat, mocetinostat, PCI-24781, entinostat, SB939, reminostat, givinostat, CUDC-101, AR-42, CHR-2845, CHR-3996, 4SC-202, CG200745, ACY-1215, sulforaphane and kevetrin.

"Inhibitors of mitochondria transition pore opening", as used herein, refer to substances that block the non-specific increase in the permeability of the inner membrane of the mithocondria, caused by the opening of an inner membrane channel. Examples of inhibitors of mitochondria transition pore opening are cyclosporin A and derivatives thereof, NIM811, 2-aminoethoxydiphenyl borate and bongkrekic acid.

"Anti-inflammatory drugs", as used herein, refer to substances that reduce inflammation. Examples of anti-inflammatory drugs are salicylates, such as acetylsalicylic acid, diflunisal and salsalate; propionic acid derivatives, such as ibuprofen, naproxen, fenoprofen, ketoprofen, dexketoprofen, flurbiprofen, oxaprozin, loxoprofen; acetic acid derivatives, such as indomethacin, sulindac, etodolac, ketorolac, diclofenac, nabumetone; enolic acid derivatives, such as piroxicam, meloxicam, tenoxicam, droxicam, lornoxicam and isoxicam; fenamic acid derivatives such as mefenamic acid, meclofenamic acid, flufenamic acid, and tolfenamic acid; selective COX-2 inhibitors such as celecoxib, rofecoxib, valdecoxib, parecoxib, lumiracoxib, etoricoxib and firocoxib; sulphonanilides such as nimesulide; and other compounds such as licofelone, monomethyl fumarate and dimethyl fumarate.

"PPAR agonists", as used herein, refer to substances that stimulate the peroxisome proliferator-activated receptors. Examples of PPAR agonists are GW-9662, thiazolidinediones, such as rosiglitazone; fibrates, such as bezafibrate, ciprofibrate, clofibrate, gemfibrozil and fenofibrate; and glitazars such as muraglitazar, tesaglitazar and aleglitazar.

"RXR agonists", as used herein, refer to substances that stimulate the retinoid X receptor. Examples of RXR agonists are CD 3254, docosahexaenoic acid, fluorobexarotene, bexarotene, retinoic acid and SR 11237.

"Sirtuin 1 agonists", as used herein, refer to substances that stimulate the sirtuin 1 enzyme. Examples of sirtuin 1 agonists are resveratrol and SRT-1720.

"Hypolipidemic agents", as used herein, refer to substances other than PPAR agonist and fibrates that lower the lipid low density lipoproteins (LDL) and/or increase the high density lipoprotein (HDL) in blood. Examples of hypolipidemic agents are statins, such as atorvastatin, cerivastatin, fluvastatin, lovastatin, mevastatin, pitavastatin, pravastatin, rosuvastatin, and simvastatin; niacin; bile acid sequestrants, such as cholestyramine, colesevelam and colestipol; other compounds such as phytosterols, ezetimibe, orlistat, and niacin.

The term "combination" as used herein, is meant to encompass the administration to a patient suffering in a patient suffering or in risk of suffering from an adrenoleukodystrophy, preferably adult adrenomyeloneuropathy (AMN), cerebral adrenomyeloneuropathy (cAMN) or the childhood variant of adrenoleukodystrophy (cALD)adrenoleukodystrophy, even more preferably adrenomyeloneuropathy (AMN), of pioglitazone, or a pharmaceutically acceptable salt thereof, and the other referred therapeutic agent previously defined, in the same or separate pharmaceutical formulations, and at the same time or at different times.

The combination drugs can be administered together, one after the other or separately in one combined unit dosage form or in two separate unit dosage forms. The unit dosage form may also be a fixed combination.

Simultaneous use (administration) may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently.

Separate use (administration) preferably means administration of the components of the combination independently of each other at different time points.

In a preferred embodiment of the invention pioglitazone, or a pharmaceutically acceptable salt thereof, and the other drug form part of the same composition.

In another preferred embodiment, pioglitazone, or a pharmaceutically acceptable salt thereof, and the other drug are provided as separate compositions for administration at the same time or at different times.

According to a second aspect, the present invention is directed to a pharmaceutical composition comprising a compound of the invention of formula (I) as defined above and a pharmaceutically acceptable excipient.

The term "excipient" refers to a diluent, adjuvant, carrier, or vehicle with which the active ingredient is administered. Such pharmaceutical excipients can be sterile liquids, such as water and oils, including those of petroleum, animal, vegetable or synthetic origin, such as peanut oil, soybean oil, mineral oil, sesame oil and the like.

Water or aqueous solution saline solutions and aqueous dextrose and glycerol solutions are preferably employed as carriers, particularly for injectable solutions, also buffers, isotonic agents or agents capable increasing solubility. Suitable pharmaceutical carriers are described in "Remington's Pharmaceutical Sciences" by E. W. Martin or "Tratado de Farmacia Galénica", C. Faulíi Trillo, Luzán 5, S.A. de Ediciones, 1993.

The pharmaceutical composition of the invention may be administered in the form of different preparations. Examples of pharmaceutical compositions include any solid (tablets, pills, capsules, granules etc.) or liquid (solutions, suspensions, syrups or emulsions) composition for oral, topical or parenteral administration.

In a preferred embodiment the pharmaceutical compositions are in oral form. Oral forms of pharmaceutical compositions may be solid or liquid. Suitable dosage forms for oral administration may be tablets, capsules, pills, granules, syrups or solutions. Preferably, the pharmaceutical composition is a solid form selected from the group consisting of tablets, capsules, pills, and granules; even more preferably, a tablet.

The solid oral pharmaceutical compositions may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycolate, hydroxypropylcellulose, carboxymethylcelluloses or microcrystalline cellulose; or pharmaceutically acceptable wetting agents such as sodium lauryl sulfate. Preferably, the excipients are selected from the group consisting of lactose monohydrate, hydroxypropylcellulose, carboxymethylcellulose calcium, and magnesium stearate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

Additional definitions

"ABCD1 protein" is a protein that transfers fatty acids into peroxisomes and is encoded by the ABCD1 gene. This protein is an adenosine triphosphate-binding cassette peroxisomal transporter involved in the import of very long chain fatty acids (VLFA) and VLCA-CoA esters into the peroxisome for degradation. "mtDNA" refers to mitochondrial DNA, which is the DNA located in the mitochondria.

"Cyt b" refers to cytochrome b, which is a component of respiratory chain complex III, which is involved in electron transport and generation of ATP.

"Cebpα" or "C/EBPα" refers to CCAAT/enhancer-binding protein alpha, which is a transcription factor.

"NDUFB8" refers to NADH dehydrogenase ubiquinone 1 beta subcomplex subunit 8 (NDUFB8) protein, which belong to the family of mitochondrial respiratory chain complex I.

"VDAC" refers to voltage-dependent anion channel protein which is a mitochondrial porin ion channel located on the outer mitochondrial membrane.

"SIRT1" SIRT1 refers to sirtuin 1 or silent mating type information regulation 2 homolog 1 (S. cerevisiae), which is a protein that is encoded by the SIRT1 gene. This enzyme deacetylates proteins that contribute to cellular regulation.

"PGC-1α" refers to peroxisome proliferator-activated receptor gamma coactivator 1-alpha, which is a protein that is encoded by the PPARGC1A gene. This coactivator regulates the genes involved in energy metabolism.

"PGC-1α" refers to peroxisome proliferator-activated receptor gamma coactivator 1-beta, which is a protein that is encoded by the PPARGC1B gene.

PGC-1α a and PGC-1β orchestrate the contents and/or activity of several transcriptional regulators of mitochondrial components including: i) nuclear hormone receptors such as PPARα/β/γ and ERRα, ii) the nuclear-encoded NRF1 and NRF2, which activate the transcription of nuclear genes encoding for respiratory and detoxifying proteins, and iii) the mitochondrial transcription factors TFAM, TFB1M and TFB2M; they control the replication and transcription of mtDNA, which in turn encodes for some subunits of the respiratory complexes (43-47). NRF1 and NRF2 induce the expression of these latter mitochondrial transcription factors (45), thus coordinating nuclear and mitochondrial events towards the complete synthesis of mitochondrial components.

"ERRα" refers to estrogen-related receptor alpha that is a nuclear receptor encoded by the ESRRA (estrogen related receptor alpha) gene. This protein regulates genes involved in mitochondrial biogenesis, gluconeogenesis, oxidative phosphorilation, and fatty acid metabolism.

"NRF 1" refers to nuclear respiratory factor 1 which activates the transcription of nuclear genes encoding for respiratory and detoxifying proteins.

"NRF2" refers to nuclear respiratory factor 2 which activates the transcription of nuclear genes encoding for respiratory and detoxifying proteins. "TFAM" refers to transcription factor A, mitochondrial, which is a protein that is encoded by the TFAM gene, and controls the replication and transcription of mtDNA.

"TFB1M" refers to dimethyladenosine transferase 1, mitochondrial, enzyme that is encoded by the TFB1M gene. This enzyme is involved in the transcription from mtDNA.

"TFB2M" refers tp dimethyladenosine transferase 2, mitochondrial, enzyme that is encoded by the TFB2M gene. This enzyme is involved in the transcription from mtDNA.

"COXII" refers to cytochrome c oxidase subunit II, which is the second subunit of cytochrome c oxidase (cytochrome c oxidase is an enzymatic complex which is a component of the respiratory chain and is involved in the transfer of electrons from cytochrome c to oxigen), which transfers the electrons from cytochrome c to the catalytic subunit 1.

The terms "Abcd1-null mice" or "Abcd1⁻ mice" refer to mice wherein the gene ABCD1 has been knocked out, i.e. made inoperative or deleted.

The term "Abcd1$^{31}$ Abcd2$^{-/-}$"refers to mice wherein the genes ABCD1 and ABCD2 have been deleted, i.e. double knockout mice (DKO). This double mutants exhibit higher VLCFA accumulation in spinal cord, higher levels of oxidative damage to proteins, and more severe AMN-like pathology, which an earlier onset than is the case with the single mutant Abcd1-null mouse.

The terms "WT" or "Wt" or "wt" refer to wild type mice, which is the phenotype o the typical form of a mouse as it occurs in nature.

EXAMPLES

The following examples are displayed to illustrate the present invention. They do not intend to limit in any way the scope of the invention defined in the present description.

The mouse models for X-ALD (Abcd1⁻ and Abcd1⁻ Abcd2$^{-/-}$ mice) exhibit a late-onset neurological phenotype with locomotor disability and axonal degeneration in spinal cords, thus it has been used as X-ALD model in the following examples.

The following examples show that mtDNA and mitochondrial protein expression are lowered in the spinal cords of Abcd1-null mice, the mouse model of X-ALD, and in the white matter of X-ALD patients, concomitant to severe alterations in the SIRT1/PGC-1α axis due to a hitherto uncovered post-translational modification of SIRT1 by oxidative stress that control mitochondria biogenesis. Orally administered pioglitazone improved mitochondria depletion, energetic failure, motor performance and axonal damage of X-ALD mice (both Abcd1⁻ and Abcd1⁻/Abcd2$^{-/-}$ mice) via an anti-oxidant effect on SIRT1 as compared to untreated control littermate groups.

Material and Methods
Antibodies

The following antibodies were used for Western Blots: anti-mouse NADH-ubiquinol oxidoreductase (NDUFB8: complex I): dilution 1/2000 (Molecular Probes); anti-mouse anti-Porin 31HL (VDAC or Voltage Dependant Anion Channel): dilution 1/1000 (Calbiochem); anti-rabbit DNP: dilution 1/100 (Invitrogen); anti-mouse PGC-1a: dilution 1/1000 (ST1202, Calbiochem); anti-rabbit SIRT1 for mouse: dilution 1/500 (12193, Abcam); anti-rabbit SIRT1 for human: dilution 1/500 (32441, Abcam) and anti-mouse γ-tubulin: dilution 1/5000 (T6557, clone GTU-88, Sigma). Goat anti-rabbit IgG linked to horseradish peroxidase, dilution: 1/15000 (P0448, Dako, Glostrup, Denmark) and Goat anti-mouse IgG linked to horseradish peroxidase, dilution: 1/15000 (G21040, Invitrogen) have been used as secondary antibodies.

Mouse Breeding

The generation and genotyping of Abcd1⁻ mice have been previously described [Pujol A. et al., Hum. Mol. Genet. 2002, 11, 499-505; and Lu J. F. et al., Proc. Natl. Acad. Sci. USA 1997, 94, 9366-9371]. The mice used for the studies were on a pure C57BL/6J background. The animals were sacrificed and the tissues were recovered and conserved at −80° C. All the methods employed in this work are in accordance with the Guide for the Care and Use of Laboratory Animals published by the US National Institutes of Health [NIH Publications No. 85-23, revised 1996], and with the ethical committee of IDI-BELL and the Generalitat de Catalunya.

Mice Treatment

We carried the studies in two animal models of AMN. The first model was the Abcd1-null mice. At 12 months of age these mice show already biochemical signs of pathology including oxidative stress [Fourcade S. et al., Hum. Mol Genet. 2008, 17, 1762-1773] and energy homeostasis alterations [Galino J. et al., Antioxid. Redox Signal 2011, 15, 2095-2107], although first clinical signs of AMN (i.e. axonopathy and locomotor impairment) appear at 20 months [Pujol A. et al., Hum. Mol. Genet. 2004, 13, 2997-3006; and Pujol A. et al., Hum. Mol. Genet. 2002, 11, 499-505]. In these mice we characterized the biochemical signs of adult X-ALD. The second model was the double knockout (DKO) mice (or Abcd1⁻/Abcd2$^{-/-}$) with removal of both Abcd1 and Abcd2 transporters. The DKO mice exhibit greater VLCFA accumulation in spinal cords [Pujol A. et al., Hum. Mol. Genet. 2004, 13, 2997-3006], higher levels of oxidative damage to proteins [Fourcade S. et al., Hum. Mol. Genet. 2010, 19, 2005-2014], and more severe AMN-like pathology, with an earlier onset (at 12 months) than is the case for the single Abcd1-null mutant [Lopez-Erauskin J. et al., Ann. Neurol. 2011, 70, 84-92; Pujol A. et al., Hum. Mol. Genet. 2004, 13, 2997-3006; Pujol A. et al., Hum. Mol. Genet. 2002, 11, 499-505; and Ferrer I. et al., Hum. Mol. Genet. 2005, 14, 3565-3577]. In these mice we assessed the clinical signs of AMN.

Pioglitazone (Actos®) was mixed into AIN-76A chow from Dyets (Bethlehem, Pa.) at 0.012% w/w, corresponding to a dose of 9 mg/kg/day per mice [Yan Q. et al., J. Neurosci. 2003, 23, 7504-7509]. Abcd1-null mice and littermate controls were treated with pioglitazone starting at 10 and a half months of age for 2 months to assess its effect on the progression of biochemical signs of X-ALD Animals were randomly assigned to one of the following dietary groups. Group I (WT): WT mice (n=12) received only normal AIN-76A chow, Group II (Abcd1⁻) Abcd1⁻ mice (n=12) received only normal AIN-76A chow, and Group III (Abcd1⁻+PIO) Abcd1⁻ mice (n=12) were treated with chow containing pioglitazone.

We set up a preclinical trial to assess the effect of pioglitazone on the progression of clinical signs using DKO null mice as the model Animals were randomly assigned to one of the following groups. Group I (WT): WT mice (n=25) received only normal AIN-76A chow, Group II (DKO) Abcd1⁻/Abcd2$^{-/-}$ mice (n=17) received only normal AIN-76A chow, and Group III (DKO+PIO) Abcd1⁻/ Abcd2$^{-/-}$ mice (n=17) were treated with chow containing pioglitazone. We treated animals for 4 months starting at 13 months of age in order to start treatment at the onset of clinical signs [Lopez-Erauskin J. et al., Ann. Neurol. 2011, 70, 84-92; Pujol A. et al., Hum. Mol. Genet. 2004, 13, 2997-3006; Pujol A. et al., Hum. Mol. Genet. 2002, 11, 499-505; and Ferrer I. et al., Hum. Mol. Genet. 2005, 14, 3565-3577]. Pioglitazone had no effect on either weight or food intake in both protocols of treatment.

Human Brain Samples

Brain necropsies from five clinically diagnosed cALD (cerebral childhood ALD) male patients, five cerAMN (cerebral adrenomyeloneuropathy) male patients, and eight healthy male control subjects, age matched (Table 1) were obtained from P. Aubourg (Department of Pediatric Neurology, Hopital Saint-Vincent de Paul, Paris, France). Informed and written consent was obtained from all patients or their legal representatives, and studies were approved y the local Ethics Committee of Hopital Saint-Vincent de Paul.

TABLE 1

Human sample characteristics. cALD is cerebral childhood ALD and cerAMN is cerebral adrenomyeloneuropathy.

| Patient code | Type | Age | Brain area |
|---|---|---|---|
| 1 | cALD | 6 | Frontal cortex |
| 2 | cALD | 9 | Frontal cortex |
| 3 | cALD | 13 | Frontal cortex |
| 4 | cALD | 13 | Frontal cortex |
| 5 | cerAMN | 27 | Frontal cortex |
| 6 | cerAMN | 39 | Frontal cortex |
| 7 | cerAMN | 39 | Frontal cortex |
| 8 | cerAMN | 43 | Parietal |
| 9 | cerAMN | 47 | Frontal cortex |

Western Blotting

Tissues were removed from euthanized mice and flash-frozen on liquid nitrogen. Frozen tissues were homogenized in RIPA buffer boiled for 5 min and centrifuged. We measured protein concentration of the supernatant with a BCA (bicinchoninic acid) Protein Assay Kit (Pierce). 10 to 100 µg were loaded onto each lane of 10% polyacrylamide gels for 60 min at 120 mV. Resolved proteins were transferred to nitrocellulose. Proteins were detected with ECL western blotting analysis system (Amersham Biosciences).

RNA and DNA Extraction

First tissues were lysed using Trizol reagent (Invitrogen), then total RNA was extracted using RNeasy Kit (Qiagen). Lysis and extraction were performed according to the manufacturer's instructions. Total DNA from tissues was extracted using Gentra Puregene Tissue Kit (Qiagen) according to the manufacturer's instructions.

Quantitative Real-Time PCR (RT-PCR)

One pg of RNA was transcribed into cDNA using Superscript II reverse transcription reagents in a final volume of 25 µl (Invitrogen). A TaqMan real time PCR was performed within the ABI PRISM 7300HT sequence detection system using the TaqMan Universal PCR master mix and the standardized primers for mouse SIRT1 (Mm00490758) PGC-1α (Mm00447183), PGC-1β (Mm01258518), ERRα (Mm00433143), NRF-1 (Mm00447996), TFAM (Mm00447485), TFB1M (Mm00524825) and TFB2M (Mm01620397). To measure gene expression and mtDNA abundance 0.1 to 0.2 µl of cDNA and 100 ng of DNA were respectively used.

To quantify mouse and human mtDNA content, two probes (mouse cytochrome b (cytb) (Gene ID: 17711) and human cytochrome c oxidoreductase subunit II (COXII) (Gene ID: 4513) were respectively designed (Custom TaqMan Gene Expression Assays; Applied Biosystems). The sequences for mouse cytb primers were: ATGACCCCAATACGCAAAATTA (SEQ ID NO: 1) (forward) and GGAGGACATAGCCTATGAAGG (SEQ ID NO: 2) (reverse) and the FAM-labeled probe was TTGCAACTATAGCAACAG (SEQ ID NO: 3). The sequences for human COXII primers were: CAAACCACTTTCACCGCTACAC (SEQ ID NO: 4) (forward) and GGACGATGGGCATGAAACTGT (SEQ ID NO: 5) (reverse) and the FAM-labeled probe was AAATCTGTGGAGCAAACC (SEQ ID NO: 6). Quantification of mtDNA was referred to nuclear DNA as determined by the amplification of the intronless nuclear gene C/EBPα. (Mouse and human CEBPα are respectively: Mm00514283, Hs00269972.). Each sample was run in duplicate, and the mean value of the duplicate was used to calculate the mRNA expression of the genes of interest which were normalized to that of the reference control (18S, Hs99999901) using the comparative ($2^{-\Delta Ct}$) method, according to the manufacturer's instructions.

SIRT1 Immunoprecipitation

Since the specific carbonylated SIRT1 antibody is not available, SIRT1 has been immunoprecipitated to measure carbonyl levels, as earlier described [Caito S. et al., *Faseb J.* 2010, 24, 3145-3159]. Protein (200 µg) extracted from whole spinal cord in a final volume of 400 µl RIPA buffer was incubated for 1 h with SIRT1 antibody [12193, (Abcam)] ((Abcam, 12193), dilution 1:80). Protein A sepharose (Amersham) was suspended in PBS for 1 h then blocked in BSA (1%) for 1 h. Protein A sepharose (50 µl) was added to each sample and left overnight at 4° C. on a rotator. The samples are then centrifuged at 13,000 rpm at 4 ° C. for 5 min. 10% SDS-PAGE were transferred to nitrocellulose membranes and derivatized with DNPH as previously described [Lopez-Erauskin J. et al., *Ann. Neural.* 2011, 70, 84-92].

SIRT1 Activity

We used a SIRT1 fluorometric assay kit (BIOMOL) based on the generation of a fluorophore via the NADtdependent deacetylation by SIRT1 of its substrate, which is a peptide comprising amino acids 379-382 of human p53 (Arg-His-Lys-Lys(Acetyl) (SEQ ID NO: 7) [Howitz K. T. et al., *Nature* 2003, 425, 191-196; and Vaziri H. et al., *Cell* 2001, 107, 149-159]. The assay's fluorescence signal is generated in proportion to the amount of Lys-382 deacetylation [Chabi B. et al., *J. Appl. Physiol.* 2009, 107, 1730-1735]. Briefly, 25 µg of total protein were incubated with Fluor de Lys-Sirt1 substrate (100 µM) and NAD+ (100 µM) at 37° C. for 30 min in a final volume of 50 µl. The reaction was stopped by the addition of 50 µl of developer reagent and nicotinamide (2 mM) and the fluorescence was subsequently monitored for 30 min at 360 nm (excitation) and 460 nm (emission).

ATP Levels, NAD-NADH Determination and Pyruvate Kinase Activity

To determine ATP levels, mice were sacrificed by cervical dislocation and spinal cords immediately frozen in liquid nitrogen and stored at −80° C. ATP was extracted with cold perchloric acid (10%) from 10 mg of spinal cord, neutralized with KOH and centrifugated [Khan H. A. et al., *J. Biosci.* 2003, 28, 379-382]. Then, ATP concentrations were quantified in triplicate per animal using the ATPlite 1 step (PerkinElmer) according to the manufacturer's protocol. Data were normalized to mg of proteins. All assays were performed in triplicate.

NAD+ and NADH were quantified by the NAD cycling assay and pyruvate kinase activity was determined by a spectrophotometrical method as previously described [Galino J. et al., *Antiox. Redox Signal* 2011, 15, 2095-2107].

Measurement of GSA (Glutamic Semialdehyde), AASA (Aminoadipic Semialdehyde), CML ($N^\epsilon$-(carboxymethyl)-lysine), CEL ($N^\epsilon$-(Carboxyethyl)-lysine), MDAL ($N^\epsilon$-(malondialdehyde)-lysine), GSA, AASA, CML, CEL, and MDAL concentrations in total proteins from spinal cord homogenates were measured by gas chromatography/mass spectrometry (GC/MS) [Lopez-Erauskin J. et al., *Ann. Neurol.* 2011, 70, 84-92; Fourcade S. et al., *Hum. Mol. Genet.* 2008, 17, 1762-1773; Fourcade S. et al., *Hum. Mol. Genet.* 2010, 19, 2005-2014; and Pamplona R. et al., *J. Biol. Chem.* 2005, 280, 21522-21530]. The amounts of products were expressed as the ratio of micromole of glutamic semialdehyde, aminoadipic semialdehyde, CML, CEL, or MDAL/mol of lysine.

Immunohistochemistry

Spinal cords were harvested from 18 month-old wild type (WT), Abcd1−/Abcd2−/− (DKO) and Abcd1−/Abcd2−/− fed with pioglitazone for 4 months (DKO+PIO), after perfusion with PFA 4%, basically as described [Lopez-Erauskin J. et al., *Ann. Neurol.* 2011, 70, 84-92; Pujol A. et al., *Hum. Mol. Genet.* 2004, 13, 2997-3006; and Ferrer I. et al., *Hum. Mol. Genet.* 2005, 14, 3565-3577]. Spinal cords were embedded in paraffin and serial sections, 5 μm thick, were cut in a transversal or longitudinal plane. The sections were stained with haematoxylin and eosin and Sudan black, or processed for immunohistochemistry to glial fibrillary acidic protein (GFAP, Dako, rabbit polyclonal, 1:500), APP (Boehringer, 1:10), synaptophysin (Dako, monoclonal, 1:500), with lectin *Lycopericon esculentum* (Sigma, L-0651, 1:200) used as a marker of microglial cells.

The number of abnormal specific profiles was counted at every 10 sections for each particular stain. At least three sections corresponding to the dorsal columns of the spinal cord were analysed per animal and per stain. Results were expressed as mean values±standard deviations.

Behavioural Testing

Treadmill Test

The treadmill apparatus (Panlab, Barcelona, Spain) consisted of a belt (50 cm long and 20 cm wide) varying in terms of speed (5 to 150 cm/s) and slope)(0-25° enclosed in a plexiglass chamber [Lopez-Erauskin J. et al., *Ann. Neurol.* 2011, 70, 84-92]. An electrified grid was located to the rear of the belt on which footshocks (0.2 mA) were administered whenever the mice fell off the belt [Lopez-Erauskin J. et al., *Ann. Neurol.* 2011, 70, 84-92].

Horizontal Bar Cross Test

The bar cross test was carried out using a wooden bar of 100 cm in length and 2 cm in width (diameter). This bar is just wide enough for the mice to stand on with their hind feet hanging over the edge such that any slight lateral misstep will result in a slip. The bar was elevated 50 cm from the bench surface, so that animals did not jump off, yet were not injured upon falling from the bar. Bar cross test was performed basically as previously described [Lopez-Erauskin J. et al., *Ann. Neurol.* 2011, 70, 84-92; and Ferrer I. et al., *Hum. Mol. Genet.* 2005, 14, 3565-3577].

Statistical Analyses

Data are given as mean +/− standard deviation (SD). Significant differences were determined by one-way ANOVA followed by Tukey HSD post-test after verifying normality ($*P<0.05$, $P<0.01$, $*P<0.001$). Statistical analyses were performed using SPSS 12.0 program.

Figure 1:
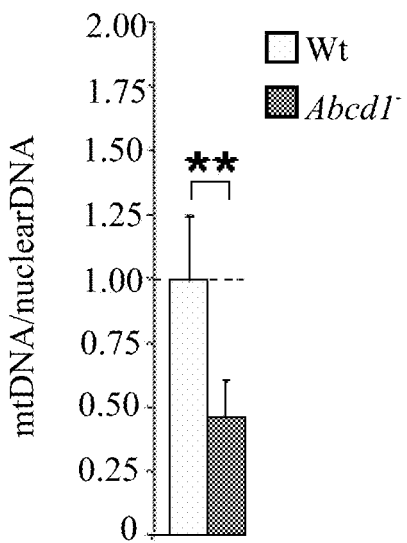

Example 1 mtDNA and Mitochondrial Protein Levels are Dpleted in Spinal Cords from Abcd1-null Mice The transcriptomic analysis of spinal cords of Abcd1-null mice has revealed a 50% repression in the expression of genes encoding for mitochondrial proteins at 12 months of age [Schlüter A. et al., *Hum Mol Genet,* 2012, 21, 1062-1077]. To investigate whether this reduction is associated with a lower amount of mitochondria we quantified: i) mtDNA as the ratio between mitochondrial cytochrome b (cytb) and nuclear C/EBPα by RT-PCR, ii) the protein contents of respiratory chain complexes I (NDUFB8) by Western blot, and iii) the protein contents of voltage-dependent anion channel VDAC by Western blot, a mitochondrial porin whose expression is found correlative to mitochondria abundance [Mahad D. J. et al., *Brain* 2009, 132, 1161-1174]. We observed a reduction of the three parameters in Abcd1-null mice respect to controls (FIG. 1 and FIG. 2), thus suggesting a mitochondrial depletion hinted at by the transcriptomic studies. Remarkably, the phenomenon is specific of spinal cords for it does not occur in the brain cortex or in liver from Abcd1-null mice at the same age (FIG. 3).

Example 2

SIRT1/PGC-1α Related Pathways are Altered in Abcd1-null Mice

We next aimed at gaining further insight into the mechanisms underlying the decrease of both mtDNA and mitochondrial protein abundance in X-ALD mice. The master regulators of mitochondria biogenesis PGC-1α □ and PGC-1β□ orchestrate the contents and/or activity of several transcriptional regulators of mitochondrial components including: i) nuclear hormone receptors such as PPARα/β/γγ and ERRα□□ estrogen-related receptor-α□□ ii) the nuclear-encoded NRF1 (nuclear respiratory factor 1) and NRF2 (nuclear respiratory factor 2), which activate the transcription of nuclear genes encoding for respiratory and detoxifying proteins, and iii) the mitochondrial transcription factors TFAM, TFB1M and TFB2M; they control the replication and transcription of mtDNA, which in turn encodes for some subunits of the respiratory complexes [Gleyzer N. et al., *Mol. Cell. Biol.* 2005, 25, 1354-1366; Lin J. et al., *Cell Metab.* 2005, 1, 361-370; Puigserver P. et al., *Cell* 1998, 92, 829-839; Wareski P. et al., *J. Biol. Chem.* 2009, 284, 21379-21385; and Wu Z. et al., *Cell* 1999, 98, 115-124]. NRF1 and NRF2 induce the expression of these latter mitochondrial transcription factors [Puigserver P. et al., *Cell* 1998, 92, 829-839], thus coordinating nuclear and mitochondrial events towards the complete synthesis of mitochondrial components. Moreover, the activity of PGC-1α is increased when it is deacetylated, which thus stimulates the rates of PGC-1α-mediated transcription. This process is preferentially due to SIRT1 [Rodgers J. T. et al., *FEBS Lett.* 2008, 582, 46-53].

We examined in X-ALD mice the expression and/or activity of key aforementioned elements participating in the pathways leading to mitochondrial biogenesis. We found that PGC-1α was reduced in spinal cords from Abcd1-null mice by RT-PCR (FIG. 4). Consistent with this, the mRNA levels of their transcriptional targets NRF1, TFAM, TFB1M and TFB2M by RT-PCR were also reduced (FIG. 4). Moreover, the mRNA and protein contents of SIRT1 by Western blot as well as its activity were reduced (FIG. 4-FIG. 6), suggesting that the functional impairment of the SIRT1/PGC-1α pathways may account for the observed depletion of mtDNA and mitochondrial protein levels.

We have identified oxidative damage as the cause of dysfunction of enzymes related to energy metabolism in X-ALD mice [Yan Q. et al., *J. Neurosci.* 2003, 23, 7504-7509]. To investigate if this would also explain the reduction in SIRT1 activity, we measured oxidative post-translational modifications. SIRT1 from spinal cords from WT and Abcd1-null mice was thus immunoprecipitated, and carbonyl modifications of the protein were then quantified by derivatizing the immunoprecipitated SIRT 1 with DNPH (dinotrophenylhydrazine) [Lopez-Erauskin J. et al., *Ann. Neurol.* 2011, 70, 84-92]. We found increased contents of carbonylated SIRT1 in Abcd1-null mice samples (FIG. 7), suggesting that oxidative stress could contribute to mitochondrial depletion via SIRT1 oxidation.

Interestingly, a reduced expression of mtDNA, SIRT1, PGC-1α,□□ NDUFB8 and VDAC was also found in the affected brain white matter of X-ALD patients (FIG. 8 and FIG. 9). This supports that lower levels of mtDNA and mitochondrial proteins associated to defective SIRT1/PGC-1α pathways may play a central role in X-ALD pathogenesis.

Example 3

Pioglitazone Prevents Decrease of mtDNA and Mitochondrial Protein Levels in Abcd1-null Mice The mtDNA content, the NUDFB8 and VDAC protein levels and the relative gene expression of SIRT1, PGC-1α, TFAM, and NRF-1 were determined in samples of spinal cord from Abcd1-null mice treated with Pioglitazone and compared with samples from both wild-type mice and untreated Abcd1-null mice. Pioglitazone normalized the mtDNA/nDNA ratio (FIG. 10), and increased both mitochondrial proteins NDUFB8 and VDAC (FIG. 11) and the contents of PGC-1-dependent factors such as NRF1 and TFAM mRNA (FIG. 12). Overall, the data are compatible with a role for pioglitazone in restoring mitochondrial biogenesis by targeting PGC-1α. Moreover, pioglitazone increased the expression of PGC-1α mRNA although it had no effect on SIRT1 expression. Remarkably, pioglitazone lowered levels of carbonylation on SIRT1 protein (FIG. 13) which rescued SIRT1 activity (FIG. 13). These results indicated a direct link between oxidative stress and levels of both mtDNA and mitochondrial proteins regulated by SIRT 1.

Example 4

Pioglitazone Rescues Metabolic Failure

The ratio $NAD^+/NADH$ is a sensitive indicator of the energy metabolism and redox state of the cell since, within the mitochondria, it links the citric acid cycle with the oxidative phosphorylation. Overall, a condition of oxidative stress and impairment of energy metabolism is reflected by decreased contents of NADH and ATP. We investigate whether pioglitazone could prevent the bioenergetic failure in Abcd1-null mice by measuring ATP, NADH and pyruvate kinase activity. We found that pioglitazone normalised the levels of ATP and NADH (FIGS. 14a and 14b), as well as the activity of pyruvate kinase (FIG. 14c) in accordance with correction of mitochondria levels.

Example 5

Pioglitazone Normalizes the Levels of Oxidative Stress Biomarkers

We quantified by GC/MS markers of oxidative lesions to proteins, which are abnormally elevated in Abcd1-null mice [Lopez-Erauskin J. et al., Ann. Neurol. 2011, 70, 84-92; and Fourcade S. et al., Hum. Mol. Genet. 2008, 17, 1762-1773]. We found that contents of GSA, AASA, CEL (glycoxidative) and MDAL (lipoxidative) were normalized by pioglitazone (FIG. 15a). In addition, antioxidant enzymes GPX1 but not SOD2, whose levels are affected in Abcd1-null mice [Hum. Mol. Genet. 2008, 17, 1762-1773], are normalized by pioglitazone (FIG. 15b).

Example 6

Pioglitazone Prevents Axonal Degeneration in Abcd1$^-$/Abcd2$^{-/-}$ Mice

Immunohistochemistry experiments were performed. Abcd1$^-$/Abcd2$^{-/-}$ (DKO) mice present an overt neuropathological phenotype at 16 months of age, characterized by: i) axonal damage as suggested by the accumulation of amyloid precursor protein (APP) and synaptophysin in axonal swellings; ii) scattered myelin debris, as revealed by Sudan black; iii) astrocytosis and microgliosis, as identified with GFAP and lectin staining, respectively, without signs of apoptosis. The most affected areas for both the axonal and the accompanying reactive glial changes are the pyramidal tracts and dorsal fascicles [Lopez-Erauskin J. et al., Ann. Neurol. 2011, 70, 84-92; and Pujol A. et al., Hum. Mol. Genet. 2004, 13, 2997-3006].

The accumulation of markers of axonal damage, as well as the number of reactive astrocytes and reactive microglia was strikingly reduced to control levels upon pioglitazone treatment during 4 months (from 13 months of age till 17 months of age (see FIG. 16, FIG. 17 and Table 2).

TABLE 2

Summary of the main pathological findings in 1 cm long longitudinal section of the dorsal spinal cord in wild type (WT), Abcd1$^-$/Abcd2$^{-/-}$ (DKO), and Abcd1$^-$/Abcd2$^{-/-}$ treated with pioglitazone during 4 months (from 13 months of age till 17 months of age (DKO + PIO) mice at 17 months of age (n = 5-6 mice per genotype and condition). DNA damage is stained with 8-oxodG, microglial cells are stained with lectin *Lycopericon esculentum* and astrocytes with GFAP.

|  | WT | DKO | DKO + PIO |
| --- | --- | --- | --- |
| 8-oxodG | * | *** | * |
| Lectin | * | *** | * |
| GFAP | * | *** | * |
| Sudan black | * | *** | * |

*Normal appearance;
**, slight and
***, marked increase in the number and size of astrocytes and microglia.
Sudan black visualizes abnormal lipidic droplets from myelin debris.

Example 7

Pioglitazone Arrests the Progression of Locomotor Deficits in Abcd1$^-$/Abcd2$^{-/-}$ Mice Mice were evaluated by the treadmill test and the bar-cross at the start and re-scored after 2 (i.e 15 months of age), and 4 months (i.e. 17 months of age) of the treatment.

In the treadmill test, training session performance was normal for all groups, indicating that the acquisition of the skill was correct (data not shown). When mice were subjected to consecutive trials at increasing speed up to 20 cm/sec and a 20° slope, no differences were detected between sessions between wild type (WT) and Abcd1$^-$/Abcd2$^{-/-}$ (DKO) mice at 17 months of age (data not shown). However, when the belt speed was 30 cm/sec and a 20° slope, differences were detected in Abcd1$^-$/Abcd2$^{-/-}$ mice compared to controls as this task requires greater coordination. This was then chosen for assessment of the effects of pioglitazone. After 2 months of treatment, the ratio between times of shock and number of shocks was significantly different between WT and DKO mice. Pioglitazone appeared to improve this ratio, but the effect was not statistically significant (FIG. 18). By contrast, the ratio was normalized after 4 months of treatment, which evidenced that pioglitazone arrests the progression of locomotor deficits in X-ALD mice (FIG. 18).

In the bar-cross experiment, double mutants on vehicle often failed to maintain their balance on the bar and fell, and they exhibited a greater tendency to slip off the bar, as well as longer time latencies to reach the platform at the opposite extreme of the bar. Some of the mice did display ventral recumbence, while wrapping laterally hind and fore limbs around the bar, as described [Lopez-Erauskin J. et al., *Ann. Neurol.* 2011, 70, 84-92; and Ferrer I. et al., *Hum. Mol. Genet.* 2005, 14, 3565-3577]. The beneficial effects of pioglitazone were striking as both parameters—the time used to cross the bar and the number of slips- reached full normalisation already after 2 months of treatment (FIG. 19).

The above experiments show that a mitochondrial dysfunction contributes to pathology in X-ALD and also that pioglitazone exerts therapeutic benefits in X-ALD and in other neurodegenerative diseases by restoring mitochondrial function.

The decreased contents of mtDNA and mitochondrial proteins detected in spinal cords of X-ALD mice as well as in brains from patients show that mitochondria are depleted in X-ALD.

The joint down-regulation in Abcd1-null mice of several transcription factors controlling the expression of structural or functional components of mitochondria points to impairment of Sirt1/PGC-1α-dependent pathways as a possible mechanism underlying decrease of mtDNA and mitochondrial protein contents. We have identified oxidation of SIRT1 as a possible culprit of PGC-1α dysfunction. SIRT1 is the best characterized member of the $NAD^+$-dependent sirtuin deacetylase family, which is increasingly recognized to regulate mechanisms that enhance homeostasis and limit susceptibility to stress and age-related degeneration. Both oxidation and SIRT1 activity are normalized by treatment with pioglitazone. These data point to SIRT1 malfunction as the possible link between oxidative damage and impaired mitochondria biogenesis in X-ALD.

As shown in the preceding examples, pioglitazone halts axonal degeneration and arrests the progression of locomotor disabilities in X-ALD.

The invention claimed is:

1. A method of treating adrenoleukodystrophies, said method comprising administering pioglitazone, or a pharmaceutically acceptable salt thereof, to a patient in need of said treatment.

2. The method of claim 1, wherein the adrenoleukodystrophy is selected from the group consisting of adult adrenomyeloneuropathy (AMN), cerebral adrenomyeloneuropathy (cAMN), and the childhood variant of adrenoleukodystrophy (cALD).

3. The method of claim 1, wherein the adrenoleukodystropahy is adult adrenomyeloneuropahy (AMN).

4. The method of claim 1, which comprises administering from 0.1 to 1.5 mg/kg/day of pioglitazone, or pharmaceutically acceptable salt thereof.

5. The method of claim 1, wherein said pharmaceutically acceptable salt is pioglitazone hydrochloride.

6. The method of claim 1, wherein the pioglitazone, or pharmaceutically acceptable salt thereof, is combined with one or more drugs selected from the group consisting of antioxidants, antioxidants targeted to mitochondria, histone deacetylase inhibitors, inhibitors of mitochondria transition pore opening, anti-inflammatory drugs, PPAR agonists, RXR agonists, sirtuin 1 agonists, hipolipidemic drugs, hypolipidemic agents, and neuroprotector drugs.

7. The method of claim 6, wherein pioglitazone, or pharmaceutically acceptable salt thereof, and the other one or more drug form part of the same composition.

8. The method of claim 6, wherein pioglitazone, or pharmaceutically acceptable salt thereof, and the other drug are provided as separate compositions for administration at the same time or at different times.

9. The method of claim 1, wherein the pioglitazone, or pharmaceutically acceptable salt thereof, is administered as a pharmaceutical composition that further comprises a pharmaceutically acceptable excipient.

10. The method of claim 9, wherein the pharmaceutical composition is for oral administration.

11. The method of claim 10, wherein said pharmaceutical composition is a solid form selected from the group consisting of tablets, capsules, pills, and granules.

* * * * *

UNITED STATES PATENT AND TRADEMARK OFFICE
CERTIFICATE OF CORRECTION

PATENT NO. : 8,865,747 B2
APPLICATION NO. : 13/799636
DATED : October 21, 2014
INVENTOR(S) : Aurora Pujol Onofre Page 1 of 1

It is certified that error appears in the above-identified patent and that said Letters Patent is hereby corrected as shown below:

Title Page, under item (30), Foreign Application Priority Data: change "March 23, 2012 (EP)...............12382108" to --March 23, 2012 (EP).............12382108.4--

Signed and Sealed this
Thirty-first Day of March, 2015

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1 atgacccaa tacgcaaaat ta                                            22

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
ggaggacata gcctatgaag g                                            21

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
ttgcaactat agcaacag                                                18

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
caaaccactt tcaccgctac ac                                           22

<210> SEQ ID NO 5
<211> LENGTH: 21
<212> TYPE: DNA
<213> ORGANISM: Artificial Sequence
<220> FEATURE:
```

```
<223> OTHER INFORMATION: Synthetic Construct

<400> SEQUENCE: 5
ggacgatggg catgaaactg t                                          21

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
aaatctgtgg agcaaacc                                              18

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: ACETYLATION

<400> SEQUENCE: 7

Arg His Lys Lys
1
```